United States Patent
Bannan et al.

(10) Patent No.: US 7,115,268 B1
(45) Date of Patent: Oct. 3, 2006

(54) PEPTIDES USEFUL FOR REDUCING SYMPTOMS OF TOXIC SHOCK SYNDROME AND SEPTIC SHOCK

(75) Inventors: Jason D. Bannan, Centreville, VA (US); Kumar Visvanathan, New York, NY (US); John B. Zabriskie, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/335,581

(22) Filed: Jun. 18, 1999

Related U.S. Application Data

(63) Continuation-in-part of application No. 09/168,303, filed on Oct. 7, 1998, now abandoned, which is a continuation-in-part of application No. 08/838,413, filed on Apr. 7, 1997, now Pat. No. 6,075,119.

(51) Int. Cl.
    *A61K 39/02*    (2006.01)
    *A61K 39/395*   (2006.01)
    *A61K 39/40*    (2006.01)
    *A61K 39/42*    (2006.01)
    *A61B 5/055*    (2006.01)

(52) U.S. Cl. ............... 424/190.1; 424/9.34; 424/130.1; 424/139.1; 424/150.1; 424/178.1; 424/184.1; 424/185.1; 424/234.1; 424/237.1; 424/243.1; 424/278.1; 435/69.3; 436/86; 530/300; 930/10; 930/200

(58) Field of Classification Search ............... 530/350, 530/300, 324, 325, 326, 327, 328, 333; 424/184.1, 424/185.1, 192.1, 244.1, 243.1, 180.1, 9.34, 424/130.1, 139.1, 150.1, 178.1, 190.1, 234.1, 424/278.1; 435/69.3; 436/86; 930/10, 200
See application file for complete search history.

(56) References Cited

U.S. PATENT DOCUMENTS 5,378,607 A    1/1995   Chelladurai et al.

(Continued)

FOREIGN PATENT DOCUMENTS

WO    WO 91/10680    7/1991

(Continued)

OTHER PUBLICATIONS

Harris, T.O. and Betley, M.J., "Biological activities of Staphylococcal-enterotoxin type-A mutants with N-Terminal Substitutions," *Infect. Immun.* 63(6):2133-2140 (1995).

(Continued)

*Primary Examiner*—Lynette R.F. Smith
*Assistant Examiner*—Ja-Na Hines
(74) *Attorney, Agent, or Firm*—John P. White, Esq.; Cooper & Dunham LLP

(57) ABSTRACT

This invention relates to compositions and methods which provide protection against, or reduce the severity of toxic shock and septic shock from bacterial infections. More particularly it relates to peptides derived from homologous sequences of the family of staphylococcal and streptococcal toxins, which may be polymeric, and carrier-conjugates thereof. The invention also relates to serum antibodies induced by the peptides and carrier-conjugates and their use to prevent, treat, or protect against the toxic effects of most, if not all, of the staphylococcal and streptococcal toxins.

The invention also relates to diagnostic assays and kits to detect the presence of staphylococcal and streptococcal toxins, or antibodies thereto. The invention also relates isolated and purified to nucleic acids encoding the peptides of the invention and transformed host cells containing those nucleic acids.

1 Claim, 11 Drawing Sheets

U.S. PATENT DOCUMENTS

| | | | |
|---|---|---|---|
| 5,437,978 A | 8/1995 | Ubukata et al. | |
| 5,470,716 A | 11/1995 | Leung et al. | |
| 5,476,767 A | 12/1995 | Leung et al. | |
| 5,519,114 A | 5/1996 | Johnson et al. | |
| 5,529,934 A | 6/1996 | Chelladurai et al. | |
| 5,545,716 A | 8/1996 | Johnson et al. | |
| 5,585,465 A | 12/1996 | Leung et al. | |
| 5,601,830 A | 2/1997 | Su et al. ................. | 424/237.1 |
| 5,705,151 A | 1/1998 | Dow et al. | |
| 5,728,388 A | 3/1998 | Terman | |
| 6,075,119 A * | 6/2000 | Bannan et al. | |

FOREIGN PATENT DOCUMENTS

| | | |
|---|---|---|
| WO | WO 93/24136 | 12/1993 |
| WO | WO 94/20124 | 9/1994 |
| WO | WO 94/25483 | 11/1994 |
| WO | WO 96/36366 | 11/1996 |
| WO | WO 96/40930 | 12/1996 |
| WO | WO 98/29444 | 7/1998 |
| WO | WO 98/45325 | 10/1998 |
| WO | WO 98/57657 | 12/1998 |

OTHER PUBLICATIONS

Hartwig, U.F.., et al., "Mutations affecting MHC class II binding of the superantigen streptococcal erythrogenic toxin A", *Intern'l Immunol.*, 5:869-75 (1993).

Hayball, J.D., et al. "The domain structure and functional relationships in the bacterial superantigen SEB, " *Biol. Chem. Hoppe-Seyler*376:303-309 (1995).

Hoffmann, M.L., et al., "Predictions of T-Cell Receptor-and Major Histocompatibility Complex-Binding Sites on Staphylococcal Enterotoxin C1", *Infect. Immun.*, 62(8):3396-3407 (1994).

Hovde, C.J., et al. "Investigation of the role of disulphide bond activity and structure of staphylococcal enterotoxin C1," *Mol. Micro.* 13(5):897-909 (1994).

Huang, I.Y., et al., "Complete amino acid sequence of staphylococcal enterotoxin A", *J. Biol. Chem.*, 262(15) 7006-7013 (1987).

Huang, I.Y., et al., "The primary structure of staphylococcal enterotoxin B. III. The cyanogen bromide peptides of reduced and aminoethylated enterotoxin B, and the complete amino acid sequence", *J. Biol. Chem.*245(14):3518-25 (1970).

Hynes, W.L., et al. "Immunologic Cross-Reactivity of Type A Streptococcal Exotoxin (Erythrogenic Toxin) and Staphylococcal Enterotoxins B and C1", *Infect. Immun.*, 55(3):837-838 (1987).

Iandolo, J.J., "Genetic analysis of extracellular toxins of Staphylococcus aureus", *Annu. Rev. Microbiol.*, 43:375-402 (1989).

Jett, M., et al., "Identification of Staphylococcal Enterotoxin B Sequences Important for Induction of Lymphocyte Proliferation by Using Synthetic Peptide Fragments of the Toxin", *Infect. Immun.*, 62(8):3408-3415 (1994).

Kline, J.B. and Collins, J.M., "Analysis of superantigenic activity of mutant and allelic forms of streptococcal pyrogenic exotoxin A," *Infect. Immun.*64(3):861-869 (Mar. 1996).

International Search Report from related application PCT/US99/ 22180, international filing date: Sep. 24,1999; claimed priority date: Oct. 7, 1998.

Bannan, J. et al., "Structure and Function of Streptococcal and Staphylococcal Superantigens in Septic Shock", *Infectious Disease Clinics of North America*, 13(2):387-396 (Jun. 1999); (mailed May 11, 1999 according to the publisher, W.B. Saunders Co.).

Fischetti, V.A. et al., "Streptococcal M Protein Extracted By Nonionic Detergent", *The Jounal of Experimental Medicine*. 144/ 1:32-53 (1976).

Griggs, N.D. et al., "Mapping of Multiple Binding Domains of the Superantigen Staphylococcal Enterotoxin A for HLA", *J. Immunol.*, 148(8):2516-2521 (1992).

Huang, I.Y. et al., "Complete amino acid sequence of staphylococcal enterotoxin A", *J. Biol. Chem.*, 262(15):7006-7013 (1987).

Pontzer, C.H. et al., "Agonist Properties of a Microbial Superantigen Peptide", *Biochem. Biophy. Res. Comm.*, 193(3):1191-1197 (1993).

Reda, K.B. et al., "Molecular Characterization and Phylogenetic Distribution of the Streptococcal Superantigen Gene (ssa) from *Streptococcus pyogenes*", *Infection and Immunity*, 62/5:1867-1874 (May 1994).

Van Den Busshe, R.A., et al., "Molecular Evolution of the Staphylococcal and Streptococcal Pyrogenic Toxin Gene Family", *Molecular Phylogenetics and Evolution*, 2:281-292 (1993).

Ren, K et al., "Characterization and Biological Properties of a New Staphylococcal Exotoxin", *J. Exp. Med.,*180:1675-1683 (Nov. 1994).

Copy of Search Report in PCT/US98/06663 (listing references and related patents).

Bannan, J. et al., "Structure and Function of Streptococcal and Staphylococcal Superantigens in Septic Shock", *Infectious Disease Clinics of North America* 13(2):387-396 (Jun. 1999); (mailed May 11, 1999 according to the publisher, W.B. Saunders Co.).

Bannan, J.D. et al., "Neutralization Of Streptococcal Pyrogenic Exotoxins And Staphylococcal Enterotoxins by Antiserum To Synthetic Peptides Representing Conserved Amino Acid Motifs", *Adv. Exp. Med. Biol.* 418:903-907 (1997); (published May 1997 in U.S. and Sep. 1997 in britain according tot he publisher's (Plenum Press, New York) catalog at http://www.plenum.com/title.cgi?0306456036).

Bavari, S. et al., "Superantigen vaccines: a comparative study of genetically attenuated receptor-binding mutants of staphylococcal enterotoxin A", *Journal of Infectious Diseases* 174(2):338-45 (1996).

Blomster-Hautamaa, E.A. et al. "Localization of biologic functions of toxic shock syndrome toxin-1 by use of monoclonal antibodies and cyanogen bromide-generated toxin fragments," *J. Immunol.* 137(11):3572-3576 (1986).

Bohach, G.A., et al., "Biological and immunological properties of the carboxyl terminus of Staphylococcal entero-toxin C1," *Infect. Immun.* 57(1):23-28 (1989).

Bonventre, P.F. et al., "A mutation at histidine residue 135 of toxic shock syndrome toxin yields an immunogenic protein with minimal toxicity, " *Infect. Immun.*63(2):509-515 (1995).

Chu, N.R. et al., "Comparison of peptide and superantigen-induced anergy in a peptide-specific polyclonal human T cell line," *Int. Immtunol.* 7(7):1057-1063 (1995).

Drynda, A., et al., "Role of a carboxy-terminal site of toxic shock syndrome toxin 1 in eliciting immune responses of human peripheral blood mononuclear cells," *Infect. Immun.* 63(3):1095-1101 (1995).

Edwin, C., et al., "Structure-activity relationship of toxic-shock-syndrome toxin-1:derivation and characterization of immunologically and biologically active fragments," *J. Infect. Dis.* 158(6):1287-1295 (1988).

Edwin,C., et al., "Specificity and cross-reactivity of staphylococcal enterotoxin A monoclonal antibodies with enterotoxins B,$C_1$ ,D, and E", *Applied & Environmental Microbiology* , 52(6): 1253-7 (1986).

Fischetti, V.A., et al., "Streptococcal M Protein Extracted By Nonionic Detergent", *The Journal of Experimental Medicine*, 144/ 1:32-53 (1976).

Griggs, N.D.., et al "Mapping of Multiple Binding Domains of the Superantigen Staphylococcal Enterotoxin A for HLA", *J. Immunol.*, 148(8):2516-2521 (1992).

Grossman, D., et al., "Mutation of the disulfide loop in staphylococcal enterotoxin-A-Consequences for T-Cell recognition," *J. Immunol.* 147(10):3274-3281 (1991).

Harris, T.O. and Betley, M.J., "Biological activities of Staphylococcal-enterotoxin type-A mutants with N-terminal substitutions," *Infect. Immun.* 63(6):2133-2140 (1995).

Hartwig, U.F., et al., "Mutations affecting MHC class II binding of the superantigen streptococcal erythrogenic toxin A", *Inter'l Immunol.*, 5:869-75 (1993).

Hayball, J.D., et al. "The domain structure and functional relationships in the bacterial superantigen SEB," *Biol. Chem. Hoppe-Seyler* 376:303-309 (1995).

Hoffmann, M.L., et al., "Predictions of T-Cell Receptor- and Major Histocompatibility Complex-Binding Sites on Staphylococcal Enterotoxin C1", *Infec. Immun.*, 62(8):3396-3407 (1994).
Hovde, C.J., et al. "Investigation of the role of disulphide bond activity and structure of staphylococcal enterotoxin C1," *Mol.Micro* 13(5):897-909 (1994).
Huang, I.Y., et al., "Complete amino acid sequence of staphylococcal enterotoxin A", *J. Biol. Chem.*, 262(15) 7006-7013 (1987).
Huang, I.Y., et al., "The primary structure of staphylococcal enterotoxin B. III. The cyanogen bromide peptides of reduced and aminoethylated enterotoxin B, and the complete amino acid sequence", *J. Biol. Chem.*, 245(14):3518-25 (1970).
Hynes, W. L., et al. "Immunologic Cross-Reactivity of Type A Streptococcal Exotoxin (Erythrogenic Toxin) and Staphylococcal Enterotoxins B and C1", *Infect Immun.* , 55(3):837-838 (1987).
Iandolo, J.J., "Genetic analysis of extracellular toxins of Staphylococcus aureus", *Annu. Rev. Microbiol.*, 43:375-402 (1989).
Jett, M., et al., "Identification of Staphylococcal Enterotoxin B Sequences Important for Induction of Lymphocyte Proliferation by Using Synthetic Peptide Fragments of the Toxin", *Infect. Immun.*, 62(8):3408-3415 (1994).
Kline, J.B. and Collins, J.M., "Analysis of superantigenic activity of mutant and allelic forms of streptococal pyrogenic exotoxin A," *Infect. Immun.*64(3):861-869 (Mar. 1996).
Lamphear, J.G., et al., "Residues near the amino and carboxyl termini of staphylococcal enterotoxin E independently mediate TCR V beta-specific interactions", *J. Immunol.*, 156(6):2178-85 (1996).
Marrack, P., et al. "The Staphylococcal Enterotoxins and Their Relatives", *Science*, vol. 248, pp. 705-711 (1990).
Norrby-Teglund, A., et al., "Plasma from patients with severe invasive group A streptococcal infections treated with normal polyspecific IgG inhibits streptococal superantigen-induced T cell proliferation and cytokine production", *J. Immunol.*, 156(8):3057-64 (1996).
Pontzer, C.H., et al., "Localization Of An Immune Functional Site On Staphylococcal Enterotoxin A Using the Synthetic Peptide Approach", *J. Immunol.*, 143(1):280-284 (1989).
Pontzer, C.H., et al., "Agonist Properties of a Microbial Superantigen Peptide", *Biochem. Biophys. Res. Comm.*, 193(3):1191-1197 (1993).
Printout from the Genetics Computer Group "Motifs" sofware (citing:Program Manual for the Wisconsin Package, Version 8, Sep. 1994, Genetics Computer Group, 575 Science Dr., Madison, WI USA 53711).
Ramesh, N., et al., "A toxic shock syndrome toxin-1 peptide that shows homology to mycobacterial heat shock protein 18 is presented as conventional antigen to T cells by multiple HLA-DR alleles," *J. Immunol.* 148(4):1025-1030 (1992).
Ramesh, N., et al., "A toxic shock syndrome toxin-1 peptide that shows homology to amino acids 180-193 of mycobacterial heat shock protein 65 is presented as conventional antigen," *Immunol. Invest.* 23(6-7):381-391 (1994).
Reda, K.B., et al., "Molecular Characterization and Phylogenetic Distribution of the Streptococcal Superantigen Gene (ssa)", *Infection and Immunity*, 62/5:1867-1874 (May 1994).
Schlievert, P.M., et al., "Molecular structure of staphylococcus and streptococcus superantigens", *J. Clin. Immunol.*, 15(6) Suppl:4S-10S (1995).
Singh, B.R., et al., "Comparative structural analysis of staphylococcal enterotoxins A and E", *J. Biol. Chem.* , 264(8):4404-11 (1989).
Singh, B.R. et al., "Structural analysis of staphylococcal enterotoxins B and $C_1$ using circular dichroism fluorescence spectroscopy", *Biochemistry*, 27(24):8735-41 (1988).
Soos, J.M. and Johnson, H.M., "Multiple binding sites on the superantigen, staphyloccal enterotoxin B, imparts versatility in binding to MHC Class II molecules," *Biochem. Biophys. Res. Comm.* 201(2):596-602 (1994).
Spero, L., et al. "Biological Activities of the Peptides of Staphylococcal Enterotoxin C Formed by Limited Tryptic Hydrolysis", *J. Biol. Chem.*, 253(24):8787-8791 (1978).
Spero, L., et al., "On the cross-reactivity of staphylococcal enterotoxins A, B, and C", *J. Immunol.*, 120:86-89 (1978).
Spero, L., et al., "Cross-Reaction between tryptic polypeptides of staphylococcal enterotoxins b and C", *J. Immunol.*, 122:1285-1289 (1979).
Sriskandan, S. et al., "Streptococcal pyrogenic exotoxin A release, distribution, and role in a murine model of fascitis and multiorgan failure due to Streptococcus pyogenes", *J. Infect. Dis.*, 173(6):1399-407 (1996).
Swaminathan, S., et al. "Crystal structure of staphylococcal enterotoxin B, a superantigen", *Nature*, 359:801-806 (1992).
Takei, S., et al. "Intravenous immunoglobulin contains specific antibodies inhibitory to activation of T cells by staphylococcal toxin superantigens", *J. Clin. Invest.*, 91:602-607 (1993).
Van Den Bussche, et al., "Molecular Evolution of the Staphylococcal and Streptococcal Pyrogenic Toxin Gene Family", Molecular Phylogenetics and Evolution, 2:281-292, (1993).
Warren, J.R., et al. "Stabilization of native structure by the closed disulfide loop of staphyloccal enterotoxin B," *Biochemica et Biophysica Acta* 359:351-363 (1974).
Woo, J., et al. "Development of mutants of Staphylococcal toxic shock syndrome toxin-1," *Molecules and Cells*, 6(1):79-85 (Feb. 1996).
Copy of slides from oral presentation by Dr. Jason Bannan at "XIII Lancefield International Symposium on Streptococci and Streptococcal Diseases, Paris, France, Sep. 16, 1996 to Sep. 20, 1996".
Copy of Search Report in PCT/US98/06663 (listing references and related patents).

* cited by examiner

| TOXIN | REGION 1 | REGION 2 |
|---|---|---|
| PEPs: | CMYGGVTEHEGN | KKNVTVQELDYKIRKYLVDNKKLY |
| SEA | 130 CMYGGVTLHDNN 141 | 171 KKNVTVQELDLQARRYLQEKYNLY 194 |
| SEB | 140 CMYGGVTEHNGN 151 | 179 KKKVTAQELDYLTRHYLVKNKKLY 202 |
| SEC | 137 CMYGGITKHEGN 148 | 178 KKSVTAQELDIKARNFLINKKNLY 201 |
| SED | 131 CTYGGVTPHEGN 142 | 172 KKNVTVQELDAQARRYLQKDLKLY 195 |
| SEE | 130 CMYGGVTLHDNN 141 | 171 KKEVTVQELDLQARHYLHGKFGLY 194 |
| SEH | 116 CLYGGITL.NSE 126 | 151 KKNVTLQELDIKIRKILSDKYKIY 174 |
| SPEA | 128 CIYGGVTNHEGN 139 | 167 KKMVTAQELDYKVRKYLTDNKQLY 190 |
| SPEC | 112 YIYGGITPAQNN 123 | 151 KDIVTFQEIDFKIRKLYMDNYKIY 174 |
| SSA | 134 CMYGGVTEHHRN 145 | 174 KKQVTVQELDCKTRKILVSRKNLY 197 |
| TSST1 | | 161 KKQLAISTLDFEIRHQLTQIHGLY 184 |

PEPTIDES USEFUL FOR REDUCING SYMPTOMS OF TOXIC SHOCK SYNDROME AND SEPTIC SHOCK

RELATED APPLICATIONS

This is a continuation-in-part application of U.S. application Ser. No. 09/168,303 filed Oct. 7, 1998, now abandoned, which is in turn a continuation-in-part of U.S. application Ser. No. 08/838,413 filed Apr. 7, 1997, now U.S. Pat. No. 6,075,119.

FIELD OF THE INVENTION

This invention relates to compositions and methods for protecting against, or reducing the severity, of toxic shock syndrome and septic shock from bacterial infections. More particularly it relates to peptides, which may be polymeric, and carrier-conjugates thereof, derived from homologous sequences of the family of staphylococcal and streptococcal pyrogenic toxins. The peptides of the invention are useful to prevent, treat, or protect against the toxic effects of bacterial toxins, including most, if not all, of the staphylococcal and streptococcal pyrogenic toxins. These are also useful to induce serum antibodies and may also be useful in diagnostic assays.

The invention also relates to antibodies induced by the peptides and/or carrier-conjugates and their use to prevent, treat, or protect against the toxic effects of bacterial toxins, including most, if not all, of the staphylococcal and streptococcal pyrogenic toxins.

The invention also relates to compositions and methods to protect against, or ameliorate the effects of, autoimmune diseases which are associated with, or are the result of, the presence of staphylococcal or streptococcal toxins.

The invention also relates to diagnostic assays and kits to detect the presence of staphylococcal and streptococcal pyrogenic toxins, or antibodies thereto.

The invention also relates to isolated and purified nucleic acids encoding the peptides of the invention and transformed host cells containing those nucleic acids.

BACKGROUND OF THE INVENTION

The pyrogenic exotoxins of Group A streptococci and the enterotoxins of *Staphylococcus aureus*, which are also pyrogenic exotoxins, constitute a family of structurally related toxins which share similar biological activities (11, 13). The staphylococcal and streptococcal pyrogenic exotoxins also share significant amino acid homology throughout their sequences (11, 19, 40). This pyrogenic exotoxin family contains nine main toxin types, and several allelic variants (subtypes) have been described. Several studies have shown that the toxins share common motifs based on immunologic cross reactivity between the toxins (26, 27). They stimulate $CD4^+$, $CD8^+$ and $\gamma\delta^+$ T cells by a unique mechanism. These toxins share the ability to bind the β chain variable region ($V_\beta$) elements on the lateral face of the T cell receptor (TCR) and simultaneously bind to the lateral face of the class II major histocompatibility complex (MHC) of antigen presenting cells (FIG. 1), causing an aberrant proliferation of specific T-cell subsets (3, 4, 12). This property of the toxins has labeled them as "superantigens" (36) since they do not interact with the MHC and TCR molecules in the manner of conventional antigens (14, 18) and produce a massive proliferation of T cells.

The variability of the sequences in the TCR-binding region and within the MHC-II-binding regions most likely provides the different suerantigen toxins their specificities for different $V_\beta$ molecules and variable affinities for MHC-II types. (69–70)

The cross-linking of TCR with MHC-II molecules by superantigens causes a profound blastogenesis of lymphocytes and antigen-presenting cells. The resulting stimulation of leukocytes leads to a significant increase in cytokine production.

Monocytes stimulated with bacterial superantigens produce the Th1 cytokines IL-2 and IFN-γ and the anti-inflammatory cytokines IL-10 and IL-1 receptor antagonist. (71). T cells activated by superantigen stimulation produce IL-12. (72). Whole preparations of peripheral blood mononuclear cells containing lymphocytes and antigen-presenting cells elicited a wide range of inflammatory cytokines in significant amounts. The generation of monocyte cytokines such as IL-1, IL-6, TNF-α, and TNF-β was dependent on the presence of T cells. (73).

Costimulatory molecules important in conventional immune responses also play a significant role in the response of immune cells to superantigens. The costimulatory T cell antigen, CD28, and its corresponding ligand on MHC-II-bearing cells, B7, contribute to superantigen mitogenicity. (74, 75). Other costimulatory molecules, such as LFA-1/ICAM-1 and VLA-4/VCAM-1, also contribute to the activation of immune cells by superantigens. (76, 77). These immunostimulatory activities of superantigens are crucial to their ability to cause injury to the host.

The bacterial toxins cause a variety of syndromes in humans. Staphylococcal enterotoxins have been implicated in staphylococcal food poisoning (26), as well as toxic shock like syndromes (1). The gene sequences and deduced amino acid sequences of at least six staphylococcal enterotoxins ("SE"): A, B, C, D, E and H, are known, i.e., SEA, SEB, SEC, SED, SEE, and SEH (19, 23). The streptococcal pyrogenic exotoxins ("SPE") have been implicated in causing the symptoms of scarlet fever and toxic shock like syndrome (8, 20, 30). The sequences of three members of this family are known: SPEA, SPEC, and SSA (5, 23, 35).

Toxic shock syndrome toxin (TSST-1) from *S. aureus* shares similar biological activity with the SE's and SPE's, however amino acid sequences of this toxin are significantly different from these two classes of toxins (2). Structural analysis suggests that, despite the differences in amino acid composition, the overall topology of TSST-1 and the SE/SPE family of toxins is similar (41). The molecular structure of SE's and SPE's has been determined by various methods. Reviews concerning the molecular structures are available (19, 62). Molecular evolution studies of the SE/SPE family of toxins suggests that the toxins can be grouped into two main clades(34). All these toxins are highly resistant to denaturation by heat and to proteases. With the exception of TSST-1, they are soluble proteins of approximately 230 amino acids and have a central disulphide loop. In contrast TSST-1 has only 194 amino acids and does not possess any cysteines.

It has been suggested that the conservation of amino acids is important to maintaining the structure necessary for the biological activity of the toxins (32). Mutations constructed in various positions throughout the SPEA and SEB molecules were sufficient to inactivate biological activity (6, 15). Mutations at various points throughout the molecules often had different effects, suggesting that functional activities could not be attributed to any one region of the toxins (7). These results suggested that a functional tertiary structure must be maintained. Chemical modifications of highly conserved histidine residues inactivated biologic activity (29). The high conservation of the disulfide loop in the SE's and SPE's suggests an important role in the structure of the SE/SPE family of toxins. Studies show the disulfide loop is required for mitogenic activity of SEA and SEB. Reduction of the disulfide loop inactivated T cell stimulatory activity, but did not affect MHC-II binding and stimulation of monocytes (54). Peptide cleavages within the loop had no effect on T-cell mitogenicity, however cleavage of conserved sequences outside the loop of SEA resulted in loss of mitogenic activity. The loop and conserved adjacent sequences appear to be associated with avidity of the toxins to the TCR, and do not contribute to the specificity of toxins for a particular $V_\beta$ type (6). Residues determining TCR $V_\beta$ specificity appear to be located within the carboxy-terminus of the SE/SPE toxins (59), while residues critical for MHC-II binding appear to be located in the amino-terminal region, and the central portion of the molecule near the disulfide loop (53). The disulfide loop and adjacent highly conserved sequences contribute to the structural integrity of the toxins, and serve to bring the TCR and MHC binding regions in functional proximity to each other (65).

The SEs are named for their ability to induce gastrointestinal illnesses upon oral intake of a few micrograms of the toxin. The clinical effect appears in 2 to 4 hours and is manifested by nausea and diarrhea. These symptoms appear to be caused by leukotrienes and histamine released from mast cells. Additionally, both the staphylococcal and streptococcal exotoxins are implicated in gram-positive shock. Although superantigen-related septic shock appears to be primarily mediated by tumor necrosis factor (TNF)-α and interleukin (IL) 12, the contribution of other cytokines cannot be discounted. (78, 79, 80).

The physiologic response to superantigens is similar to septic shock induced by gram-negative endotoxin (lipopolysaccharide, LPS). In fact, LPS and superantigens can work synergistically to produce lethal toxic shock. (81, 82, 83). Toxic shock syndrome can be exacerbated by the synergistic effects of TSST-1 with the SE/SPE family of toxins. (84, 85). Superantigen stimulation of immune cells can exacerbate autoimmune syndromes by causing the expansion of autoreactive T cell subsets, upregulation of MHC-II expression, and the potentiation of cytotoxic T cell response (86, 87, 88, 89, 90, 91).

Toxic shock syndrome is a specific syndrome caused by either the Stapylococcal or Streptococcal organisms. It is specifically caused by the toxins produced by these bacteria. Clinically it often occurs in young women and children and is characterized by a raised temperature, low blood pressure, a rash that eventually leads to skin loss especially on the palms and the soles and multi-organ involvement.

Septic Shock on the other hand involves both gram negative as well as gram positive organisms, occurs in all groups of patients especially the elderly and post-surgical. It has similar symptoms except for the lack of a skin losing rash. Both diseases have a high mortality-however there are many more cases of septic shock as compared to toxic shock. The term "septic shock" is used herein to describe hypotension and organ failure associated with bacterial infections.

"Toxic shock like syndrome" is the term previously used to describe the syndromes caused by staphyloccal and streptococcal pyrogenic bacterial exotoxins other than toxic shock syndrome toxin (TSST-1) from *S. aureus*. Currently, the term "toxic shock syndrome" is used to describe the syndromes caused by TSST-1 and the other pyrogenic exotoxins, and is the terminology used hereinafter.

Toxic shock syndrome can be exacerbated by the synergistic effects of TSST-1 with the enterotoxin/pyrogenic toxin family of toxins (9, 25). Gram negative bacterial endotoxin and the pyrogenic toxins can work synergistically to produce intractable shock (17, 30).

With respect to septic shock, lipopolysaccharide (LPS) is an integral part of the cell wall of Gram-negative bacteria and is a potent inducer of cytokine release by macrophages (52). During the induction phase of septicemia, LPS binds to the CD14 receptors of macrophages and triggers the release of a number of cytokines including Interleukin-1 (IL-1), and Tumor Necrosis Factor-α(TNF-α) (49). Accordingly, therapeutic strategies for septic shock have centered on the neutralization of LPS or LPS-induced cytokines (64). Unfortunately, trials using either monoclonal antibodies directed against part of the LPS molecule or the use of CD14 soluble receptors have not been very promising (45). The reasons for these failures might be: 1. The type of patient selected (many were already in irreversible shock). 2. The monoclonal antibody did not block all sites of LPS. 3. Soluble CD14 receptors did not block all LPS molecules.

Toxic shock syndrome and septic shock are still among the most life threatening syndromes affecting humans. It is estimated that approximately 20,000 cases of toxic shock syndrome occur each year of with a 10% mortality rate (66). With respect to septic shock approximately 400,000–500,000 cases occur each year with a 50% mortality (63). Present therapy is primarily symptomatic with administration of fluids, antibiotics, pressor agents and occasionally steroids (56). There is no vaccine available for toxic shock syndrome since all of the superantigens are antigenically distinct even though there is some sequence homology present in all the superantigens. There have been numerous vaccine trials for septic shock none of which have been successful.

With respect to the failed vaccine trials for septic shock, we believe that there was a failure to recognize that the interaction between the superantigens described above and LPS enhances the lethal potency of both these antigens by about 1000 fold. In contrast, each antigen when given alone requires a much higher dose for lethal septic shock (46).

Hence, it is proposed that at least two independent pathways of lethal septic shock can occur. LPS and peptidoglycan interact with macrophages. The superantigens interact with T cells. In both cases target cells are induced to release large amounts of cytokines. There is increasing evidence that gram-positive infections frequently accompany gram-negative infections in patients with septic shock (see article by Rangel-Frausto, pages 299–312) (96). Exposure to gram-negative endotoxin produces a state of macrophage hyperesponsiveness on subsequent stimulation (92). A similar state is seen with monocytes in septic shock. Our group and others have shown that LPS and superantigens can act synergistically to produce lethal septic shock in animal models (93). It is our hypothesis that a significant amount of septic shock involves an early gram-negative infection that causes significant symptoms of vasodilation and hypotension. This is then treated with fluids and antibiotics, leading to early recovery by the patient. Some days later, a gram-positive insult either via a line sepsis of the skin or gastrointestinal flora may cause severe irreversible shock in a previously LPS-sensitized patient. This model is depicted graphically in FIG. 2 herein (94).

In other words, since Gram-negative and Gram-positive organisms can be recovered from patients with sepsis, it appears that it is the "two hit" hypothesis that is operative and the interaction between LPS and the superantigens markedly enhances the lethal properties of both molecules. In this model, the interruption of the toxin pathway by anti-peptide antibody(ies) or by peptide(s) of the invention prevents the onset of lethal shock induced by the combination of the LPS and one or more of the superantigens.

SUMMARY OF THE INVENTION

The present invention relates to the identification of consensus sequences derived from two conserved regions of the staphylococcal enterotoxins and streptococcal pyrogenic toxins (hereinafter called "region 1" and "region 2") and the discovery that compositions comprising amino acid sequences based on these two conserved regions of the staphylococcal enterotoxins and streptococcal pyrogenic exotoxins are capable of inducing antibodies which react with a variety of staphylococcal and streptococcal pyrogenic exotoxins and are also capable of ameliorating or preventing diseases related to the deleterious effects of these toxins.

The invention also relates to compositions and methods for preventing and treating diseases related to the release of certain pyrogenic exotoxins from bacteria.

This invention provides peptides comprising amino acid sequences which reduce, inhibit or eliminate the deleterious effects of bacterial toxins and/or are capable of inducing antibodies that reduce, inhibit or eliminate the deleterious effects of bacterial toxins, such as those of *staphylococcus* and a variety of streptococci. Antibodies may be induced by administration of a pharmaceutical composition and/or vaccine containing a composition comprising a peptide derived from one or both of the two conserved regions described herein, or a structurally and/or immunologically related antigen.

The amino acid sequences provided by this invention are sufficiently common to all members of this family of pyrogenic exotoxins to be useful for eliciting antibodies which are cross-reactive with toxins derived from various bacteria.

The amino acid sequences provided by this invention are also useful for new methods of preventing and treating symptoms associated with the bacterial release of the staphylococcal enterotoxins and the streptococcal pyrogenic exotoxins. Such methods include, for example, administering to an individual who is suspected of having an infection or developing and/or having a toxic or septic reaction, a compound comprising at least one of the consensus amino acid sequences of this invention in an amount sufficient to inhibit superantigen stimulation of T-cells, preferably an amount sufficient to reduce, inhibit or eliminate the deleterious effects of the exotoxins. Such methods also include administering to an individual at risk of infection or developing a toxic reaction to the exotoxins at least one of the consensus amino acid sequences of this invention in an amount sufficient to elicit the production of antibodies to the exotoxins.

In a preferred embodiment of this invention, an individual at risk for developing toxic or septic shock syndrome or an individual with symptoms of toxic shock syndrome or septic shock may be treated by administering to such individual a composition comprising at least one of the peptides of this invention and/or carrier-conjugate thereof.

In another preferred embodiment of this invention, an individual at risk for developing toxic shock syndrome or septic shock, or an individual with symptoms of toxic shock syndrome or septic shock, may be treated by administering to such individual antibodies which have been generated in a mammal immunized with at least one of the compositions of this invention.

Vaccines and pharmaceutical compositions comprising at least one of the consensus amino acid sequences and a physiologically acceptable carrier and optionally an adjuvant are also part of this invention.

Another object of the invention is to provide antibodies induced by the peptides and carrier-conjugates thereof. These antibodies may be used to prevent, treat, or protect against the toxic effects of most, if not all, of the staphylococcal and streptococcal pyrogenic exotoxins. The antibodies may also be useful to protect against, or ameliorate the effects of, autoimmune diseases which are associated with, or are the result of, the presence of staphylococcal or streptococcal pyrogenic exotoxins. These antibodies are also useful in diagnostic assays and kits to detect the presence of staphylococcal and streptococcal pyrogenic exotoxins and to aid in the diagnosis of diseases related to the presence of those toxins.

Another object of the invention is to provide isolated and purified nucleic acids encoding the amino acid sequences of the invention, as well as suitable expression systems, vector components and transformed host cells containing those nucleic acids.

BRIEF DESCRIPTION OF THE DRAWINGS

FIG. 3. Comparison of the synthetic peptide sequences (SEQ ID NO:3, region 1; and SEQ ID NO:4, region 2) to conserved regions 1 and 2 of the Staphylococcal enterotoxins (SEA (SEQ ID NO:9, region 1; and SEQ ID NO:18, region 2), SEB (SEQ ID NO:10, region-1; and SEQ ID NO:19, region 2), SEC (SEQ ID NO:11, region 1; and SEQ ID NO:20, region 2), SED (SEQ ID NO:12, region 1; and SEQ ID NO:21, region 2), SEE (SEQ ID NO:13, regional; and SEQ ID NO:22, region 2), and SHE (SEQ ID NO:14, region 1; and SEQ ID. NO:23, region 2)), and streptococcal pyrogenic exotoxins (SPEA (SEQ ID NO:15, region 1; and SEQ ID. NO:24, region 2), SPEC (SEQ ID NO:16, region 1; and SEQ ID NO:25, region 2) and SSA (SEQ ID NO:17, region 1; and SEQ ID NO:26, region 2)). Staphylococcal toxic shock syndrome toxin 1 (TSST-1, SEQ ID NO:27) was compared with the region 2 peptide. Numbers represent the residue positions as a reference to where these regions exist in the whole toxin molecules. Sequences are from either the Swiss protein or GenBank databases under the foilowing accession numbers. Swiss protein: SPEA, P08095; SPEC, P13380; SEA, P13163; SEB, P01552; SEC, P01553; SED, P20723; SEE, P12993. GenBank: SEH, U11702; SSA, L29565; TSST1, J02615.

DETAILED DESCRIPTION OF THE INVENTION

Figure 1:
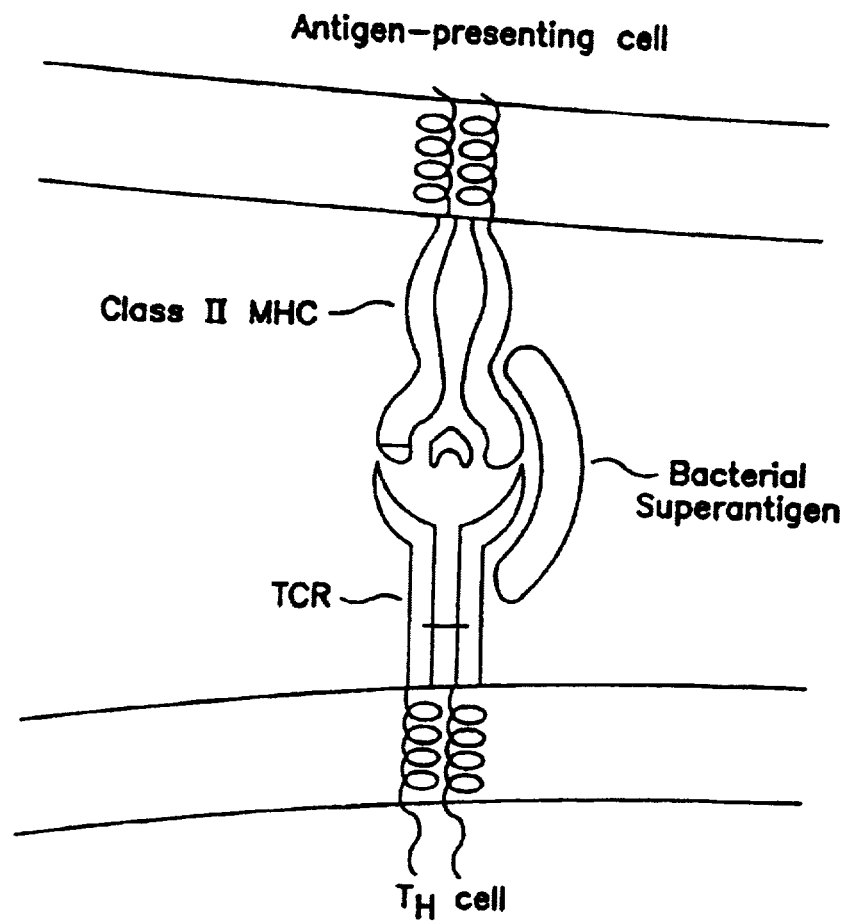
FIG. 1. Schematic diagram of the interaction between a T cell receptor, superantigen, and a class II MHC molecule. Superantigens bind to common sequences in class II MHC molecules and T cell receptors that lie outside the normal antigen-binding sites. T cell activation by superantigens is not limited by the antigenic specificity of the T cell.

It is to be understood that both the foregoing general description and the following detailed description are exemplary and explanatory only, and are not restrictive of the invention, as claimed. The accompanying drawings, which are incorporated in and constitute a part of the specification, illustrate an embodiment of the invention and, together with the description, serve to explain the principles of the invention.

Two consensus patterns, corresponding to conserved region 1 and region 2, respectively, are identified as common to members of the staphylococcal enterotoxin and streptococcal pyrogenic toxin family of toxins when the program "Motifs" in a software package from the Genetics Computer Group, Inc. ("GCG") is run using the streptococcal SPEC toxin as an example. "Program Manual for the Wisconsin Package, Version 8, September 1994, Genetics Computer Group, 575 Science Drive, Madison, Wis., USA 53711", incorporated herein by reference.

The first consensus sequence ("GCG consensus #1") identified by the Motifs program has the amino acid sequence YGG(LIV)TXXXXN, which is rewritten herein as $YGGX_1TX_2X_3X_4X_5N$ (SEQ ID NO: 1), wherein $X_1$ is selected from the group consisting of L, I, or V; and $X_2$, $X_3$, $X_4$ and $X_5$ are each independently selected from the group consisting of any amino acid. This pattern is present in the staphylococcal enterotoxins and streptococcal pyrogenic exotoxins, but not in TSST-1. The sequence begins immediately at the COOH-terminal side of the cysteine loop. The second consensus sequence ("GCG consensus #2") identified by the Motifs program has the amino acid sequence KXX(LIV)XXXX(LIV)DXXXRXXLXXXXX(LIV)Y, rewritten herein as $KX_6X_7X_8X_9X_{10}X_{11}X_{12}X_{13}DX_{14}X_{15}X_{16}RX_{17}X_{18}LX_{19}X_{20}X_{21}X_{22}X_{23}X_{24}Y$ (SEQ ID NO: 2), wherein $X_8$, $X_{13}$ and $X_{24}$ are each independently selected from the group consisting of L, I and V, and $X_6$, $X_7$, $X_9$, $X_{10}$, $X_{11}X_{12}$, $X_{14}$, $X_{15}$, $X_{16}$, $X_{17}$, $X_{18}X_{19}X_{20}$, $X_{21}$, $X_{22}$ and $X_{23}$ are each independently selected from the group consisting of any amino acid. This pattern is present in the staphylococcal enterotoxins, streptococcal pyrogenic exotoxins, and TSST-1.

One object of the invention is to provide compositions comprising peptides comprising amino acid sequences based on these two conserved regions of the staphylococcal enterotoxins and streptococcal pyrogenic toxins. These peptides may be used for eliciting an immunogenic response in mammals, including responses which provide protection against, or reduce the severity, of toxic shock or septic shock from staphylococcal or streptococcal infections. These peptides may also be useful to protect against, or ameliorate the effects of, autoimmune diseases which are associated with, or are the result of, the presence of staphylococcal or streptococcal pyrogenic exotoxins. These peptides are also useful in diagnostic assays and kits to detect the presence of antibodies to staphylococcal and streptococcal pyrogenic exotoxins and to aid in the diagnosis of diseases related to the presence of those toxins.

The peptides of the invention are those derived from either one or both of the following two consensus sequences: $YGGX_1TX_2X_3X_4X_5N$ (SEQ ID NO:1), wherein $X_1$ is selected from the group consisting of L, I, or V; and $X_2$, $X_3$, $X_4$ and $X_5$ are each independently selected from the group consisting of any amino acid. KXX(LIV)XXXX(LIV) DXXXRXXLXXXXX(LIV)Y, rewritten herein as $KX_6X_7X_8X_9X_{10}X_{11}X_{12}X_{13}DX_{14}X_{15}X_{16}RX_{17}X_{18}LX_{19}X_{20}X_{21}X_{22}X_{23}X_{24}Y$ (SEQ ID NO: 2), wherein $X_8$, $X_{13}$ and $X_{24}$ are each independently selected from the group consisting of L, I and V, and $X_6$, $X_7$, $X_9$, $X_{10}$, $X_{11}$, $X_{12}$, $X_{14}$, $X_{15}$, $X_{16}$, $X_{17}$, $X_{18}$, $X_{19}$, $X_{20}$, $X_{21}$, $X_{22}$ and $X_{23}$ are each independently selected from the group consisting of any amino acid.

A preferred consensus sequence of the invention from Region 1 (consensus #1a) has the amino acid sequence $X_{25}X_{26}YGGX_1TX_2X_3X_4X_5N$ (SEQ ID NO: 28), wherein $X_1$ is selected from the group consisting of L, I, and V; $X_2$, $X_4$ and $X_5$ are each independently selected from the group consisting of any amino acid; and $X_3$, $X_{25}$ and $X_{26}$ are each independently selected from the group consisting of any amino acid and of no amino acid; but preferably $X_1$ is selected from the group consisting of I and V; $X_2$ is selected from the group consisting of L, E, K, P and N; $X_3$ is selected from the group consisting of H and A and no amino acid; $X_4$ is selected from the group consisting of D, N, E, Q, and H; $X_5$ is selected from the group consisting of N, G, S, and R; $X_{25}$ is selected from the group consisting of C and Y and no amino acid; and $X_{26}$ is selected from the group consisting of M, T, L, I, and no amino acid.

A preferred consensus sequence of the invention from region 2 (consensus #2a) has the amino acid sequence: $KX_6X_7X_8X_9X_{10}X_{11}X_{12}X_{13}DX_{14}X_{15}X_{16}RX_{17}X_{18}X_{27}X_{19}X_{20}X_{21}X_{22}X_{23}X_{24}Y$ (SEQ ID NO: 29), wherein $X_8$, $X_{13}$ and $X_{24}$ are each independently selected from the group consisting of L, I and V; $X_6$, $X_7$, $X_9$, $X_{10}$, $X_{11}$, $X_{12}$, $X_{14}$, $X_{15}$, $X_{16}$, $X_{17}$, $X_{18}$ $X_{19}$, $X_{20}$, $X_{21}$, $X_{22}$, and $X_{23}$ are each independently selected from the group consisting of any amino acid; and $X_{27}$ is selected from the group consisting of L and Y; but preferably $X_6$ is selected from the group consisting of K and D; $X_7$ is selected from the group consisting of N, K, S, E, M, I and Q; $X_8$ is selected from the group consisting of L and V; $X_9$ is selected from the group consisting of T and A; $X_{10}$ is selected from the group consisting of V, A, L, F and I; $X_{11}$ is selected from the group consisting of Q and S; $X_{12}$ is selected from the group consisting of E and T; $X_{13}$ is selected from group consisting of L and I; $X_{14}$ is selected from the group consisting of L, Y, I, A, F and C; $X_{15}$ is selected from the group consisting of Q, L, K and E; $X_{16}$ is selected from the group consisting of A, T, I and V; $X_{17}$ is selected from the group consisting of R, H, N and K; $X_{18}$ is selected from the group consisting of Y, F, I, L and Q; $X_{19}$ is selected from the group consisting of Q, V, I, H, S, T and M; $X_{20}$ is selected from the group consisting of E, K, N, G, D, S and Q; $X_{21}$ is selected from the group consisting of K, N, D, R and I; $X_{22}$ is selected from the group consisting of Y, K, L, F and H; $X_{23}$ is selected from the group consisting of N, K, G and Q; $X_{24}$ is selected from the group consisting of L and I; and $X_{27}$ is L.

The following Table 1 lists the amino acids that are found at each of the variable positions in the sequences shown in FIG. 3, and the number of times they appear at that position:

TABLE 1

Frequency of the amino acids in the variable positions in the sequences shown in FIG. 3

| | | | | | | | |
|---|---|---|---|---|---|---|---|
| $X_1$ | 6V | 3I | | | | | |
| $X_2$ | 3L | 2E | 1K | 2P | 1N | | |
| $X_3$ | 7H | 1A | | one deletion (no amino acid) | | | |
| $X_4$ | 2D | 2N | 3E | 1Q | 1H | | |
| $X_5$ | 3N | 4G | 1S | 1R | | | |
| $X_6$ | 9K | 1D | | | | | |
| $X_7$ | 3N | 1K | 1S | 1E | 1M | 1I | 1Q |
| $X_8$ | 9V | 1L | | | | | |
| $X_9$ | 9T | 1A | | | | | |
| $X_{10}$ | 4V | 3A | 1L | 1F | 1I | | |
| $X_{11}$ | 9Q | 1S | | | | | |
| $X_{12}$ | 9E | 1T | | | | | |
| $X_{13}$ | 9L | 1I | | | | | |
| $X_{14}$ | 2L | 2Y | 2I | 1A | 2F | 1C | |
| $X_{15}$ | 3Q | 1L | 5K | 1E | | | |
| $X_{16}$ | 4A | 2T | 3I | 1V | | | |
| $X_{17}$ | 2R | 3H | 1N | 4K | | | |
| $X_{18}$ | 5Y | 1F | 2I | 1L | 1Q | | |
| $X_{19}$ | 2Q | 2V | 1I | 1H | 1S | 2T | 1M |
| $X_{20}$ | 1E | 2K | 1N | 1G | 3D | 1S | 1Q |
| $X_{21}$ | 4K | 3N | 1D | 1R | 1I | | |

TABLE 1-continued

Frequency of the amino acids in the variable positions in the sequences shown in FIG. 3

| | | | | | |
|---|---|---|---|---|---|
| $X_{22}$ | 3Y | 4K | 1L | 1F | 1H |
| $X_{23}$ | 3N | 4K | 2G | 1Q | |
| $X_{24}$ | 8L | 2I | | | |
| $X_{25}$ | 8C | 1Y | | | |
| $X_{26}$ | 5M | 2I | 1L | 1T | |
| $X_{27}$ | 9L | 1Y | | | |

In the peptides of the present invention, $X_1$, $X_8$, $X_{13}$ and $X_{24}$ may each independently be selected from the group consisting of L, I and V; $X_2$, $X_3$, $X_4$, $X_5$, $X_6$, $X_7$, $X_9$, $X_{10}$, $X_{11}$, $X_{12}$, $X_{14}$, $X_{15}$, $X_{16}$, $X_{17}$, $X_{18}$ $X_{19}$, $X_{20}$, $X_{21}$, $X_{22}$, $X_{23}$, $X_{25}$ and $X_{26}$ may each independently be any amino acid; $X_3$, $X_{25}$ and $X_{26}$ may also each independently be no amino acid; and $X_{27}$ is selected from the group consisting of L and Y. However, in general, the amino acids present at the positions $X_1$ to $X_{27}$ in the toxins shown in FIG. 3 (and listed in Table 1) are preferred for those positions, and the amino acids present most often at those positions in the toxins shown in FIG. 3 (and listed in Table 1) are more preferred. For example, from FIG. 3, and Table 1, it can be determined that H (histidine) is present in seven toxins at position $X_3$ and A (alanine) is present in one toxin at position $X_3$, and there is no amino acid present in one toxin at $X_3$. These are the preferred amino acids for position $X_3$. The more preferred amino acid for position $X_3$ in a peptide of the invention is H (histidine). The more preferred amino acids for $X_1$ through $X_{26}$ are: $X_1$=valine; $X_2$=leucine; $X_3$=histidine; $X_4$=glutamic acid; $X_5$=glycine; $X_6$=lysine; $X_7$=asparagine; $X_8$=valine; $X_9$=threonine; $X_{10}$=valine; $X_{11}$=glutamine; $X_{12}$=glutamic acid; $X_{13}$=leucine; $X_{14}$=leucine, tyrosine, isoleucine or phenylalanine; $X_{15}$=lysine; $X_{16}$=alanine; $X_{17}$=lysine; $X_{18}$=tyrosine; $X_{19}$=glutamine, valine or threonine; $X_{20}$=aspartic acid; $X_{21}$=lysine; $X_{22}$=lysine; $X_{23}$=lysine; $X_{24}$=leucine; $X_{25}$=cysteine; $X_{26}$=methionine; and $X_{27}$=leucine. But note that in the exemplified peptides of the invention described hereinbelow, i.e., SEQ ID NOS: 6, 7 and 8, inosine (I) is used at position $X_{16}$ instead of the more frequently found alanine (A).

As is evident from FIG. 3 and the above Table 1, some amino acid residues are much more highly conserved than suggested by the GCG package data provided by the "Motifs" program.

In region 1, the preferred consensus is larger (consensus #1a), and usually includes a C in the first position ($X_{25}$). The second residue ($X_{26}$) is most often a M, but this can vary. In the ninth position ($X_3$), H is the most highly conserved. The eleventh residue ($X_5$) is most often a G.

In region 2, the preferred consensus (consensus #2a) is much more highly conserved than suggested by the GCG program, especially if one excludes TSST-1 sequences from consideration, as follows: The second position ($X_6$) is more highly conserved than suggested, being almost exclusively a K; the fourth residue ($X_8$) is always a V followed exclusively by a T in the fifth position ($X_9$); the sixth position ($X_{10}$) is somewhat variable; but the seventh position ($X_{11}$) is always a Q, followed by E ($X_{12}$) The next position is almost always an L ($X_{13}$), and the second to last position ($X_{24}$) is almost always an L.

Thus, additional modified consensus sequences for region 1 and region 2, which are of narrower scope than the GCG consensus sequences #1 and #2 and the modified consensus sequences #1a and #2a, are as follows:

Consensus #1b:
CMYGGX$_1$TX$_2$HX$_4$GN (SEQ ID NO: 30)
wherein
X$_1$ is V or I, preferably V;
X$_2$ is L, E, K, P or N, preferably E or L; and
X$_4$ is D, N, E, Q or H, preferably E.
Consensus #2b:
KKX$_7$VTX$_{10}$OQELDX$_{14}$×15X$_{16}$RX$_{17}$X$_{18}$X$_{27}$X$_{19}$X$_{20}$X$_{21}$X$_{22}$X$_{23}$LY (SEQ ID NO: 31)
wherein
X$_7$ is N, K, S, E, M, I or Q, preferably N;
X$_{10}$ is V, A, L, F or I, preferably V;
X$_{14}$ is L, Y, I, A, F or C, preferably Y;
X$_{15}$ is Q, L, K or E, preferably K;
X$_{16}$ is A, T, I or V, preferably I;
X$_{17}$ is R, H, N or K, preferably K;
X$_{18}$ is Y, F, I, L or Q, preferably Y;
X$_{19}$ is Q, V, I, H, S, T or M, preferably V;
X$_{20}$ is E, K, N, D, G, S or Q, preferably D;
X$_{21}$ is K, N, D, R or I, preferably N;
X$_{22}$ is Y, K, L, F or H, preferably K;
X$_{23}$ is N, K, G or Q, preferably K; and
X$_{27}$ is L or Y, preferably L.

Peptides exemplified herein are CMYGGVTEHEGN (SEQ ID NO: 3), CMYGGVTEHEGNGC* (SEQ ID NO: 5), KKNVTVQELDYKIRKYLVDNKKLY (SEQ ID NO: 4), CGKKNVTVQELDYKIRKYLVDNKKLYGC* (SEQ ID NO: 6), CMYGGVTEHEGNKKNVTVQELDYKIRKYLVDNKKLY (SEQ ID NO: 7) and CMYGGVTEHEGNKKNVTVQELDYKIRKYLVDNKKLYGC* (SEQ ID NO: 8), wherein an asterisk indicates that the peptide is a randomly cross-linked polymer. The exemplified polymer peptides are at least 6,000 to 8,000 daltons. The average size of the exemplified polymer peptides is about 12,000 to 15,000 daltons. Small peptides and/or contaminants may be removed by dialysis or other methods available in the art. Similarly, larger aggregates may be removed using, e.g., a 0.25 micron filter, which can also be used to sterilize the peptides.

Note that the amino acids cysteine and methionine, "CM", are present at the amino terminus of the exemplified region 1 peptides since those amino acids are most often found in that position in nature. Note also that the amino acids cysteine and glycine, "CG" and "GC", are used at the amino and/or carboxy-termini of some of the exemplified region 2 peptides. The amino acid cysteine "C" is used to facilitate cross-linking through the formation of disulfide bonds. The amino acid glycine, "G", is used as a spacer residue.

The preferred peptides of the invention are those which exclude full length native toxin molecules. The preferred peptides of this invention are not toxic, but toxic peptides maybe useful in this invention, for example, in eliciting antibodies in a non-human system. The most preferred peptides of the invention do not contain amino acid sequences in the sequence in which they are found in any particular native toxin molecule.

The present invention encompasses monomers of the peptides derived from either one or both of the two consensus regions described herein. These monomers may comprise one or more sequences derived from either region 1 or region 2 or both, such as consensus sequences #1 and #2, preferably consensus sequences #1a and/or #2a, more preferably consensus sequences #1b and/or #2b, most preferably one or more of the exemplified consensus sequence peptides. If the monomer contains more than one consensus sequence, these sequences may be immediately adjacent to each other or separated by a linker. In addition, different orientations of the peptides are within the scope of this invention. Furthermore, the order of the consensus peptides within the full peptide may be variable.

The present invention also encompasses homogeneous or heterogeneous polymers of the peptides disclosed herein (e.g., concatenated, cross-linked and/or fused identical peptide units or concatenated, cross-linked and/or fused diverse peptide units), and mixtures of the peptides, polymers, and/or conjugates thereof.

Linkers useful in the invention may, for example, be simply peptide bonds, or may comprise amino acids, including amino acids capable of forming disulfide bonds, but may also comprise other molecules such as, for example, polysaccharides or fragments thereof.

In the peptides exemplified herein, sequences derived from consensus region 1 and consensus region 2 may be immediately adjacent to each other, linked by peptide bonds, (see, e.g., SEQ ID NO:7) and/or connected via amino acid linkers capable of forming di-sulfide bonds via cysteine residues (see, e.g., SEQ ID NO: 8). In the native toxin molecules, the sequences of region 1 and region 2 are separated by about 27 amino acids. When the linkers are additional amino acids, they are most preferably 1 to 27 amino acids in length, although longer linkers may also be used in accordance with this invention.

The linkers for use with this invention may be chosen so as to contribute their own immunogenic effect which may be either the same, or different, than that elicited by the consensus sequences of the invention. For example, such linkers may be bacterial antigens which also elicit the production of antibodies to infectious bacteria. In such instances, for example, the linker may be a protein or protein fragment of an infectious bacteria, or a bacterial polysaccharide or polysaccharide fragment.

A peptide of the invention includes any substituted analog or chemical derivative of a peptide derived from one or both of the two consensus regions described herein, most preferably of the exemplified peptides described herein, so long as the peptide is capable of inhibiting binding of staphylococcal and streptococcal pyrogenic exotoxins to the MHC complex; inhibiting blastogenesis of human mononuclear cells in the presence of any one of the toxins; eliciting the production of antibodies capable of binding to most of the staphylococcal and streptococcal pyrogenic exotoxins; or reacting with (i.e., specifically binding to) antibodies that react with most of the staphylococcal and streptococcal pyrogenic exotoxins. Therefore, a peptide can be subject to various changes that provide for certain advantages in its use. For example, D amino acids can be substituted for L amino acids to increase in vivo stability of the peptides, while still retaining biological activity. See, e.g., Senderoff et al. (1998) (95). Likewise, retro-inverso peptides, which contain NH—CO bonds instead of CO—NH peptide bonds, are much more resistant to proteolysis than L-peptides. Moreover, they have been shown to mimic natural L-peptides with respect to poly- and monoclonal antibodies (48). Therefore, peptides having at least one D amino acid on the amino terminal and/or carboxy terminal end of the molecule and which retain biological activity are considered part of the invention. In addition, retro-inverso peptides which contain one or more of the amino acid sequences of the invention and which retain biological activity are also considered part of the invention.

The peptides of the invention are useful for providing active immunization for the prevention of disease related to the deleterious effects of staphylococcal and streptococcal pyrogenic exotoxins and for preparation of antibodies as a passive immunization therapy. When used to prepare antibodies, the peptides are designed to induce antibodies which react with a variety of staphylococcal and streptococcal pyrogenic exotoxins (preferably with at least two, more preferably with at least four, and most preferably with at least seven of the pyrogenic exotoxins) for use in therapy to increase resistance to, prevent and/or treat toxic shock syndrome and septic shock.

The peptides may also be useful to protect against, or ameliorate the effects of, autoimmune diseases which are associated with, or are the result of, the presence of staphylococcal or streptococcal exotoxins.

The peptides of the invention will also be useful in diagnostic tests for detecting antibodies to staphylococcal and streptococcal pyrogenic exotoxins.

The peptide may be mixed with an adjuvant. The peptide also may be bound to a non-toxic non-host protein carrier to form a conjugate or it may be bound to a saccharide carrier and/or a non-toxic non-host protein carrier to form a conjugate.

The molecular weight of the peptide monomers having one consensus sequence of the invention range from about 1000 to 5000 daltons. Such lower molecular weight species of the invention are useful themselves to inhibit superantigen induced T cell proliferation and/or reduce, inhibit or eliminate the deleterious effects of bacterial exotoxins in vivo, either when used alone or in combination with another form of therapy, e.g., anticytokine antibodies.

Such lower molecular weight species of the invention may also be useful as immunogens themselves or, more preferably, may be used as haptens conjugated to a larger carrier molecule, such as, for example, a protein. As with other peptides, the molecular weight of the peptide alone, or when conjugated to a carrier, or in the presence of an adjuvant, is related to its immunogenicity. Thus, the peptide may vary in molecular weight in order to enhance its antigenicity or immunogenicity. In an exemplified embodiment, the molecular weight of the peptide, in polymeric form, is greater than about 6000 to 8000 daltons, with an average weight of 12,000 to 15,000 daltons. The total size of the peptide is only limited to its ability to be physiologically tolerated.

The invention also relates to isolated and purified nucleic acid molecules which code for the peptides of the invention to produce the encoded peptides. The encoded peptides may be monomers, polymers or linked to other peptide sequences (e.g., they may be fusion proteins). Other features of the invention include vectors which comprise the nucleic acid molecules of the invention operably linked to promoters, as well as cell lines, such as prokaryotic (e.g., *E. coli*) and eukaryotic (e.g., CHO and COS) cells transfected with the nucleic acid molecules of the invention. Vectors and compositions for enabling production of the peptides in vivo, i.e., in the individual to be treated or immunized, are also within the scope of this invention.

The nucleic acids encoding the peptides of the invention can be introduced into a vector such as a plasmid, cosmid, phage, virus or mini-chromosome and inserted into a host cell or organism by methods well known in the art. In general, the vectors containing these nucleic acids can be utilized in any cell, either eukaryotic or prokaryotic, including mammalian cells (e.g., human (e.g., HeLa), monkey (e.g., COS), rabbit (e.g., rabbit reticulocytes), rat, hamster (e.g., CHO and baby hamster kidney cells) or mouse cells (e.g., L cells), plant cells, yeast cells, insect cells or bacterial cells (e.g., *E. coli*). The vectors which can be utilized to clone and/or express these nucleic acids are the vectors which are capable of replicating and/or expressing the nucleic acids in the host cell in which the nucleic acids are desired to be replicated and/or expressed. See, e.g., F. Ausubel et al., *Current Protocols in Molecular Biology*, Greene Publishing Associates and Wiley-Interscience (1992) and Sambrook et al. (1989) for examples of appropriate vectors for various types of host cells. Strong promoters compatible with the host into which the gene is inserted may be used. These promoters may be inducible. The host cells containing these nucleic acids can be used to express large amounts of the protein useful in pharmaceuticals, diagnostic reagents, vaccines and therapeutics.

The nucleic acids could be used, for example, in the production of peptides for diagnostic reagents, vaccines and therapies for pyrogenic exotoxin related diseases. For example, vectors expressing high levels of peptide can be used in immunotherapy and immunoprophylaxis, after expression in humans. Such vectors include retroviral vectors and also include direct injection of DNA into muscle cells or other receptive cells, resulting in the efficient expression of the peptide, using the technology described, for example, in Wolff et al., *Science* 247:1465–1468 (1990), Wolff et al., *Human Molecular Genetics* 1(6):363–369 (1992) and Ulmer et al., *Science* 259:1745–1749 (1993). See also, for example, WO 96/36366 and WO 98/34640.

In another embodiment of this invention antibodies are provided which react with peptides of the invention, as well as a variety of staphylococcal and streptococcal pyrogenic exotoxins (preferably with at least two, more preferably with at least four, and most preferably with at least seven of the pyrogenic exotoxins). These antibodies will be useful for passive immunization therapy to increase resistance to or prevent toxic shock syndrome or septic shock or other diseases related to the presence of bacterial pyrogenic exotoxin. The antibodies may also be useful to protect against, or ameliorate the effects of, autoimmune diseases which are associated with, or are the result of, the presence of staphylococcal or streptococcal pyrogenic exotoxins. The antibodies of the invention will also be useful in diagnostic tests and kits for detecting the presence of staphylococcal and streptococcal pyrogenic exotoxins. These uses are discussed in more detail below.

Methods for Preparing Peptides of the Invention

The peptides of the invention may be prepared by synthetic methods or by recombinant DNA methods, as known in the art and as described herein.

Pharmaceutical Compositions

The pharmaceutical compositions of this invention contain a pharmaceutically and/or therapeutically effective amount of at least one peptide and/or carrier thereof, antibody, or nucleic acid encoding a peptide of this invention. In one embodiment of the invention, the effective amount or peptide per unit dose is an amount sufficient to inhibit T-cell proliferation by staphylococcal and/or streptococcal pyrogenic exotoxins. In another embodiment of the invention, the effective amount of peptide per unit dose is an amount sufficient to prevent, treat or protect against the toxic effects of bacterial toxins, including diarrhea and/or cardiopulmonary depression or lethal shock. The effective amount of peptide per unit dose depends, among other things, on the species of mammal inoculated, the body weight of the mammal and the chosen inoculation regimen, as is well known in the art.

In such circumstances, inocula for a human or similarly sized mammal typically contain peptide concentrations of 100 to 500 mgs/kg, body weight of the mammal per inoculation dose.

Preferably, the route of inoculation of the peptide will be subcutaneous or intravenous. The dose is administered at least once.

When the peptide of the invention is used as immunogen, the pharmaceutical composition contains an effective, immunogenic, amount of peptide of the invention. The effective amount of peptide per unit dose sufficient to induce an immune response depends, among other things, on the species of mammal inoculated, the body weight of the mammal and the chosen inoculation regimen, as well as the presence or absence of an adjuvant, as is well known in the art. Inocula typically contain peptide concentrations of about 1 microgram to about 1000 micrograms per inoculation (dose), preferably about 3 micrograms to about 100 micrograms per dose, most preferably about 5 micrograms to 50 micrograms. The use of higher amounts is envisaged. In Example 1, rabbits were injected twice with 500 micrograms of polymeric peptide in the presence of adjuvant. In Example 5, an example in which the peptide is administered directly to prevent toxic or septic shock, which may not be dependent on the production of antibodies, mice were injected twice with 1.5 mg of monomer peptide for a total of 3 mgs. Standard procedures to determine dose response relationships known to those skilled in the art may be used to determine optimum doses of peptide to be used either to prevent or treat toxic or septic shock, or to raise antibodies for its prevention or treatment.

The term "unit dose" as it pertains to the inocula refers to physically discrete units suitable as unitary dosages for mammals, each unit containing a predetermined quantity of active material (e.g., peptide, antibody or nucleic acid) calculated to produce the desired immunogenic effect in association with the required diluent.

Inocula are typically prepared as a solution in a physiologically acceptable carrier such as saline, phosphate-buffered saline and the like to form an aqueous pharmaceutical composition.

The peptides of the invention are generally administered with a physiologically acceptable carrier or vehicle therefor. A physiologically acceptable carrier is one that does not cause an adverse physical reaction upon administration and one in which the antibodies are sufficiently soluble and retain their activity to deliver a therapeutically effective amount of the compound. The therapeutically effective amount and method of administration of a peptide of the invention may vary based on the individual patient, the indication being treated and other criteria evident to one of ordinary skill in the art. A therapeutically effective amount of a peptide of the invention is one sufficient to attenuate the dysfunction without causing significant side effects such as non-specific T cell lysis or organ damage. The route(s) of administration useful in a particular application are apparent to one or ordinary skill in the art.

Routes of administration of the peptides include, but are not limited to, parenteral, and direct injection into an affected site. Parenteral routes of administration include but are not limited to intravenous, intramuscular, intraperitoneal and subcutaneous. The route of inoculation of the peptides of the invention is typically parenteral and is preferably intramuscular, sub-cutaneous and the like.

The present invention includes compositions of the peptides described above, suitable for parenteral administration including, but not limited to, pharmaceutically acceptable sterile isotonic solutions. Such solutions include, but are not limited to, saline and phosphate buffered saline for nasal, intravenous, intramuscular, intraperitoneal, subcutaneous or direct injection into a joint or other area.

A system for sustained delivery of the peptides of the invention may also be used. For example, a delivery system based on containing a peptide in a polymer matrix of biodegradable microspheres may be used (57). One such polymer matrix includes the polymer poly(lactide-co-glycolide) (PLG). PLG is biocompatible and can be given intravenously or orally. Following injection of the microspheres into the body, the encapsulated protein is released by a complex process involving hydration of the particles and drug dissolution. The duration of the release is mainly governed by the type of PLG polymer used and the release of modifying excipients (44).

The dose is administered at least once. When a composition of the invention is used to induce antibodies, at least one booster dose may be administered after the initial injection, preferably at about 4 to 6 weeks after the first dose, in order to increase the antibody level. Subsequent doses may be administered as indicated.

To monitor the antibody response of individuals administered the compositions of the invention, antibody titers may be determined. In most instances it will be sufficient to assess the antibody titer in serum or plasma obtained from such an individual. Decisions as to whether to administer booster inoculations or to change the amount of the composition administered to the individual may be at least partially based on the titer.

The titer may be based on either an immunobinding assay which measures the concentration of antibodies in the serum which bind to a specific antigen, i.e. peptide or toxin; or bactericidal assays which measure the ability of the antibodies to participate with complement in killing bacteria. The ability to neutralize in vitro and in vivo biological effects of the pyrogenic exotoxins may also be assessed to determine the effectiveness of the treatment. See, e.g., the examples herein.

Antibodies

The term "antibodies" is used herein to refer to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', $F(ab')_2$ and F(v) as well as chimeric antibody molecules.

An antibody of the present invention is typically produced by immunizing a mammal with an immunogen or vaccine containing one or more peptides of the invention, or a structurally and/or antigenically related molecule, to induce, in the mammal, antibody molecules having immunospecificity for the immunizing peptide or peptides. The peptide(s) or related molecule(s) may be monomeric, polymeric, conjugated to a carrier, and/or administered in the presence of an adjuvant. The antibody molecules may then be collected from the mammal if they are to be used in immunoassays or for providing passive immunity.

The antibody molecules of the present invention may be polyclonal or monoclonal. Monoclonal antibodies may be produced by methods known in the art. Portions of immunoglobulin molecules may also be produced by methods known in the art.

The antibody of the present invention may be contained in various carriers or media, including blood, plasma, serum (e.g., fractionated or unfractionated serum), hybridoma supernatants and the like. Alternatively, the antibody of the present invention is isolated to the extent desired by well known techniques such as, for example, by using DEAE Sephadex, or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibody of the IgG class are preferred for purposes of passive protection.

The presence of the antibodies of the present invention, either polyclonal or monoclonal, can be determined by various assays. Assay techniques include, but are not limited to, immunobinding, immunofluorescence (IF), indirect immunofluorescence, immunoprecipitation, ELISA, agglutination and Western blot techniques.

The antibodies of the present invention have a number of diagnostic and therapeutic uses. The antibodies can be used as an in vitro diagnostic agent to test for the presence of various staphylococcal and streptococcal pyrogenic exotoxins in biological samples in standard immunoassay protocols and to aid in the diagnosis of various diseases related to the presence of bacterial pyrogenic exotoxins. Preferably, the assays which use the antibodies to detect the presence of bacterial pyrogenic exotoxins in a sample involve contacting the sample with at least one of the antibodies under conditions which will allow the formation of an immunological complex between the antibody and the toxin that may be present in the sample. The formation of an immunological complex if any, indicating the presence of the toxin in the sample, is then detected and measured by suitable means. Such assays include, but are not limited to, radioimmunoassays, (RIA), ELISA, indirect immunofluorescence assay, Western blot and the like. The antibodies may be labeled or unlabeled depending on the type of assay used. Labels which may be coupled to the antibodies include those known in the art and include, but are not limited to, enzymes, radionucleotides, fluorogenic and chromogenic substrates, cofactors, biotin/avidin, colloidal gold and magnetic particles. Modification of the antibodies allows for coupling by any known means to carrier proteins or peptides or to known supports, for example, polystyrene or polyvinyl microliter plates, glass tubes or glass beads and chromatographic supports, such as paper, cellulose and cellulose derivatives, and silica.

Such assays may be, for example, of direct format (where the labelled first antibody reacts with the antigen), an indirect format (where a labelled second antibody reacts with the first antibody), a competitive format (such as the addition of a labelled antigen), or a sandwich format (where both labelled and unlabelled antibody are utilized), as well as other formats described in the art. In one such assay, the biological sample is contacted to antibodies of the present invention and a labelled second antibody is used to detect the presence of staphylococcal and streptococcal pyrogenic exotoxins, to which the antibodies are bound.

The antibodies of the present invention are also useful as therapeutic agents in the prevention and treatment of diseases caused by the deleterious effects of staphylococcal and streptococcal pyrogenic exotoxins.

The antibodies are generally administered with a physiologically acceptable carrier or vehicle therefor. A physiologically acceptable carrier is one that does not cause an adverse physical reaction upon administration and one in which the antibodies are sufficiently soluble and retain their activity to deliver a therapeutically effective amount of the compound. The therapeutically effective amount and method of administration of the antibodies may vary based on the individual patient, the indication being treated and other criteria evident to one of ordinary skill in the art. A therapeutically effective amount of the antibodies is one sufficient to inhibit superantigen stimulation of T-cells and/or attenuate the dysfunction caused by the presence of bacterial toxins without causing significant side effects such as non-specific T cell lysis or organ damage. The route(s) of administration useful in a particular application are apparent to one or ordinary skill in the art.

Routes of administration of the antibodies include, but are not limited to, parenteral, and direct injection into an affected site. Parenteral routes of administration include but are not limited to intravenous, intramuscular, intraperitoneal and subcutaneous.

The present invention includes compositions of the antibodies described above, suitable for parenteral administration including, but not limited to, pharmaceutically acceptable sterile isotonic solutions. Such solutions include, but are not limited to, saline and phosphate buffered saline for nasal, intravenous, intramuscular, intraperitoneal, subcutaneous or direct injection into a joint or other area.

Antibodies for use to elicit passive immunity in humans are preferably obtained from other humans previously inoculated with compositions comprising one or more of the consensus amino acid sequences of the invention. Alternatively, antibodies derived from other species may also be used. Such antibodies used in therapeutics suffer from several drawbacks such as a limited half-life and propensity to elicit an immune response. Several methods have been proposed to overcome these drawbacks. Antibodies made by these methods are encompassed by the present invention and are included herein. One such method is the "humanizing" of non-human antibodies by cloning the gene segment encoding the antigen binding region of the antibody to the human gene segments encoding the remainder of the antibody. Only the binding region of the antibody is thus recognized as foreign and is much less likely to cause an immune response. An article describing such antibodies is Reichmann et al., "Reshaping Human Antibodies for Therapy", Nature 332:323–327 (1988), which is incorporated herein by reference. See also, Queen et al., U.S. Pat. No. 5,585,089, which is incorporated herein by reference.

In providing the antibodies of the present invention to a recipient mammal, preferably a human, the dosage of administered antibodies will vary depending upon such factors as the mammal's age, weight, height, sex, general medical condition, previous medical history and the like.

In general, it is desirable to provide the recipient with a dosage of antibodies which is in the range of from about 5 mg/kg to about 20 mg/kg body weight of the mammal, although a lower or higher dose may be administered. In general, the antibodies will be administered intravenously (IV) or intramuscularly (IM). Intravenous immunoglobulin (IVIG) can generally be given with a loading dose of 200 mg/kg, with monthly injections of 100 mg/kg. High-dose IVIG may be given at 400–800 mg/kg for antibody-deficient patients. See, e.g., The Merck Manual of Diagnosis and Therapy, 16th Edition, (Berkow R and Fletcher A J, Eds.), Merck Research Laboratories, Rahway, N.J. (1992).

The peptides and/or antibodies of the present invention are intended to be provided to the recipient subject in an amount sufficient to prevent, or attenuate the severity, extent or duration of the deleterious effects of staphylococcal and streptococcal pyrogenic exotoxins.

The administration of the agents including peptide and antibody compositions of the invention may be for either "prophylactic" or "therapeutic" purpose. When provided prophylactically, the agents are provided in advance of any symptom. The prophylactic administration of the agent serves to prevent or ameliorate any subsequent deleterious effects of staphylococcal and streptococcal pyrogenic exotoxins. When provided therapeutically, the agent is provided at (or shortly after) the onset of a symptom of infection with bacteria expressing staphylococcal or streptococcal pyrogenic exotoxins. The agent of the present invention may, thus, be provided either prior to the anticipated exposure to bacteria expressing staphylococcal or streptococcal pyrogenic exotoxin (so as to attenuate the anticipated severity, duration or extent of disease symptoms) or after the initiation of the infection. The agent may also be provided to individuals at high risk for getting an infection with bacteria expressing staphylococcal or streptococcal pyrogenic exotoxins.

Also envisioned are therapies based upon vectors, such as viral vectors containing nucleic acid sequences coding for the peptides described herein. These molecules, developed so that they do not provoke a pathological effect, will stimulate the immune system to respond to the peptides.

For all therapeutic, prophylactic and diagnostic uses, the peptide of the invention, alone or linked to a carrier, as well as antibodies and other necessary reagents and appropriate devices and accessories may be provided in kit form so as to be readily available and easily used.

Where immunoassays are involved, such kits may contain a solid support, such as a membrane (e.g., nitrocellulose), a bead, sphere, test tube, rod, and so forth, to which a receptor such as an antibody specific for the target molecule will bind. Such kits can also include a second receptor, such as a labelled antibody. Such kits can be used for sandwich assays to detect toxins. Kits for competitive assays are also envisioned.

The following examples illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

EXAMPLE 1

Peptides whose sequences are based on the two highly conserved regions of the staphylococcal and streptococcal pyrogenic exotoxins described herein were constructed. The sequences were based on alignments of the streptococcal pyrogenic exotoxins with the staphylococcal enterotoxins, and the amino acids used in positions with possible degeneracy were the amino acids most frequently found in these positions. Three of the peptides were then catenated and polymerized to produce peptides of greater than 8000 daltons (i.e., peptides 6343, 6345 and 6348, described below). As described further below, peptide 6348 was used to immunize rabbits, which produced high titer antibodies to this peptide. These antibodies were tested for the ability to recognize the streptococcal and staphylococcal pyrogenic exotoxins. Immunological assays (immunoblots) revealed that these antibodies recognized regions common to all the pyrogenic exotoxins. These antibodies were also tested for the ability to neutralize in vitro and in vivo biological activity of the pyrogenic exotoxins. These antibodies protected against the biological T-cell proliferation of these toxins in an in vitro blastogenesis assay using human mononuclear cell populations. The lethal effects of staphylococcal toxin SEB and streptococcal pyrogenic toxin SPEA in vivo were also completely blocked by mixing the antibodies with the toxin prior to injection.

Materials and Methods

Construction of Synthetic Peptides:

Peptides were constructed by solid phase synthesis (20) using the modifications described by Houghton (10).

| | | | |
|---|---|---|---|
| 1. | GCG Consensus #1 | YGGX$_1$TX$_2$X$_3$X$_4$X$_5$N | (SEQ ID NO:1) |
| | peptide #1 | CMYGGVTEHEGN | (SEQ ID NO:3) |
| 2. | GCG Consensus #2 | KX$_6$X$_7$X$_8$X$_9$X$_{10}$X$_{11}$X$_{12}$X$_{13}$DX$_{14}$X$_{15}$X$_{16}$RX$_{17}$X$_{18}$ LX$_{19}$X$_{20}$X$_{21}$X$_{22}$X$_{23}$X$_{24}$Y | (SEQ ID NO:2) |
| | peptide #2 | KKNVTVQELDYKIRKYLVDNKKLY | (SEQ ID NO:4) |

As is evident above, synthetic peptides #1 and #2 are not native peptides, i.e., their sequences differ from those found in native toxins. Variations of these peptides have also been constructed in order to generate concatenated polymers of the peptides. These polymers were constructed by the addition of glycine and of additional cysteine residues to the amino- and/or carboxyl-termini of the initial 2 peptides, thus facilitating concatenation via disulfide bond formation (37, 38, 39). The polymerized molecules were then dialyzed to remove molecules with molecular weights less than 6000–8000 daltons. One polymeric construct is composed of the monomer: CMYGGVTEHEGNGC (SEQ ID NO:5). An additional polymer is composed of the peptide: CGKKNVTVQELDYKIRKYLVDNKKLYGC (SEQ ID NO:6).

In the native toxin molecules, consensus region #1 precedes consensus region #2 by 27 amino acid residues (e.g. [consensus region 1 ] ×27 [consensus region 2]). We have constructed the peptide: CMYGGVTEHEGNKKNVTVQELDYKIRKYLVDNKKLY (SEQ ID NO:7). Like the native toxin molecule, this peptide is representative of the two consensus regions joined together in the proper order (region 1 in the N terminal half, and region 2 in the C-terminal half of the molecule), however they are not separated by an additional 27 residues as they are in the native toxins. We have also constructed concatenated polymers based on the monomer: CMYGGVTEHEGNKKNVTVQELDYKIRKYLVDNKKLYGC (SEQ ID NO:8).

| ID# | Peptide | |
|---|---|---|
| 6343 | CMYGGVTEHEGN | (SEQ ID NO:3) |
| 6344 | CMYGGVTEHEGNGC* | (SEQ ID NO:5) |
| 6345 | KKNVTVQELDYKIRKYLVDNKKLY | (SEQ ID NO:4) |

-continued

| ID# | Peptide | |
|---|---|---|
| 6346 | CGKKNVTVQELDYKIRKYLVDNKKLYGC* | (SEQ ID NO:6) |
| 6347 | CMYGGVTEHEGNKKNVTVQELDYKIRKYLVDNKKLY | (SEQ ID NO:7) |
| 6348 | CMYGGVTEHEGNKKNVTVQELDYKIRKYLVDNKKLYGC* | (SEQ ID NO:8) |

Peptides with an (*) are cross-linked polymers composed of the described sequence. It is expected that monomers of these peptides will also be useful in the present invention.

Generation of Anti-Peptide Sera.

New Zealand White rabbits were immunized by subcutaneous injection with 500 µg of peptide in complete Freund's adjuvant. Additional booster injections of 500 µg in incomplete adjuvant was administered 4 weeks after the primary injections. Ten days after booster injections, the rabbits were bled, and the anti-peptide titers were determined by ELISA.

Staphylococcal enterotoxins, TSST-1, and streptococcal pyrogenic exotoxins were purchased from Toxin Technology Inc. (Sarasota, Fla.).

Immunoblots

Each of the staphylococcal and streptococcal pyrogenic exotoxins were electrophoresed through 10% SDS PAGE gels (16) and transferred to nitrocellulose for western blots (33). The western blots were developed using the rabbit anti-peptide 6348 serum (anti-pep 6348 or AP6348) diluted 1:5000, followed by goat anti-rabbit (IgG) alkaline phosphate conjugate (Sigma).

Inhibition of Blastogenesis

Human peripheral blood mononuclear cell (PBMC) preparations were stimulated by each of the staphylococcal enterotoxins and streptococcal pyrogenic exotoxins. 100 ng of toxin was used to stimulate PBMC preparations at cell concentrations of $10^5$ cells per well in 96 well microliter plates. Phytohemagglutinin (PHA) was used in place of the toxins as a positive mitogenic control. Cell culture medium was supplemented with either 10% normal rabbit serum (NRS) or AP6348 serum. Blastogenesis was assayed by incorporation of tritiated thymidine after 5 days of culture (22). All experiments were performed in triplicate.

Passive Protection of Rabbits

Female New Zealand White rabbits >1 yr old were obtained from Hazelton Dutchland Labs, Inc. (Denver, Pa.). Rabbits were challenged with staphylococcal or streptococcal toxins at doses ranging from 50 to 100 µg/kg, as previously described (24). Briefly, pyrogenic toxins were incubated with either 200 ul of normal rabbit serum or 200 ul of anti-pep #6348 serum for one hour prior to challenge. Toxin-serum mixtures were administered intravenously through the marginal ear veins. Normal control rabbits were treated in an identical manner, with isotonic saline substituted for the pyrogenic toxin. Four hours later, rabbits were given a sub-lethal dose (5 µg/kg) of endotoxin (E. coli LPS, List Biological Laboratories, Inc., Campbell, Calif.). Rabbits were monitored 72 h for clinical signs of toxic shock. These included elevated temperature, diarrhea, cardiopulmonary distress, and conjunctival injection. Rabbits with severe toxic shock exhibiting cyanosis and temperatures less than 97° F. were declared moribund. Moribund rabbits were euthanized by administration of 5 ml pentobarbital sodium. All animal protocols were reviewed by the Laboratory Animal Research Center at the Rockefeller University.

Results

ELISA Assays

Figure 4:
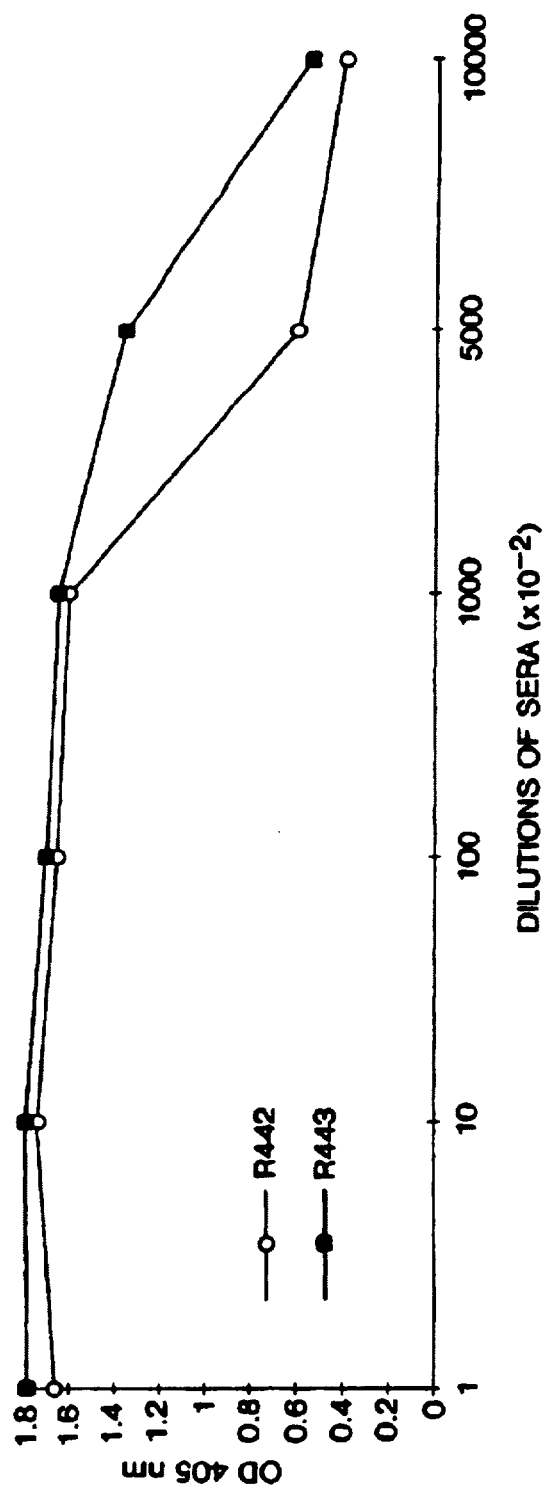
FIG. 4. ELISA titers of antibodies from rabbits immunized with polymeric peptide #6348. The peptide was diluted so that it was delivered to each well to give a final concentration of 2 μg/100 μl. The serum was then diluted to 1:1,000; 1:10,000; 1:100,000; 1:500,000; and 1:1,000,000 and 100 μl of each dilution of serum was placed in each well. Experiments were run in triplicate for each dilution of serum. Note the 1 log higher titers of rabbit #443 serum as compared to rabbit #442 serum. Cut off readings were at O.D. 0.6.

As seen in FIG. 4, rabbits raised significant antibody titers to peptide 6348. Similarly, rabbits receiving immunizations with peptides 6344 and 6346 also developed high titers.

Recognition of Staphylococcal and Streptococcal Toxins by Anti-Pep 6348 Serum

Figure 5:
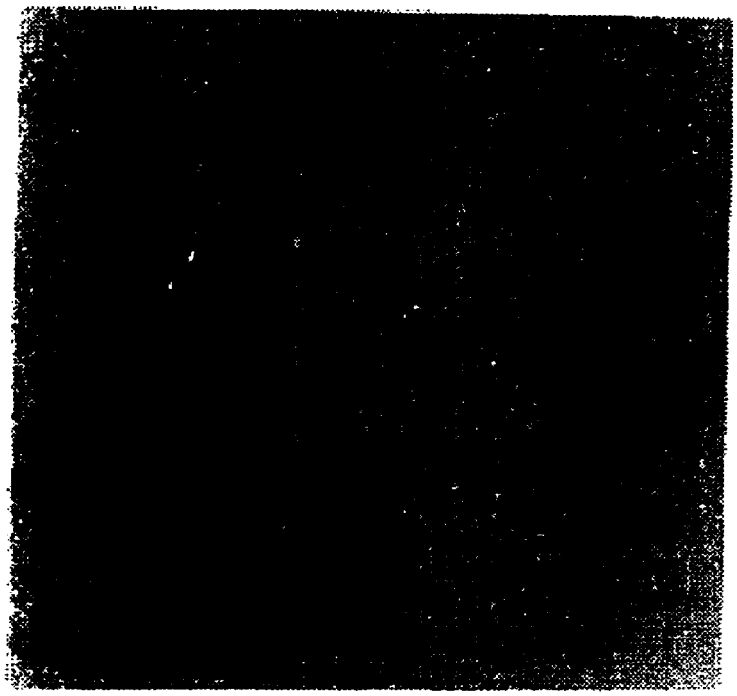
FIG. 5. 12% SDS PAGE gel immunoblot of a variety of staphylococcal and streptococcal toxins developed with the anti-peptide 6348 antibody. Note bands of correct molecular weight (M.W.) of each toxin identified by the anti-peptide antibody. Lane 1: SPEA, lane 2: SEA, lane 3: SEB, lane 4: SED, lane 5: SEE, lane 6: SEC and lane 7 TssT-1. Note bands at appropriate M.W. in lanes 1–4. Fainter bands are seen in lanes 5 and 7.

Western blots of the staphylococcal and streptococcal toxins were developed with anti-peptide 6348 serum followed by an anti-rabbit IgG alkaline phosphatase conjugate (Sigma). The results of the western blot shown in FIG. 5 indicate the anti-peptide 6348 serum recognizes the conserved regions of the bacterial toxin molecules; SEA, SEB, SED, SEE, SPEA, and TSST-1. SEC did not show a significant reaction with anti-peptide 6348.

Blastogenesis Inhibition

Figure 6:
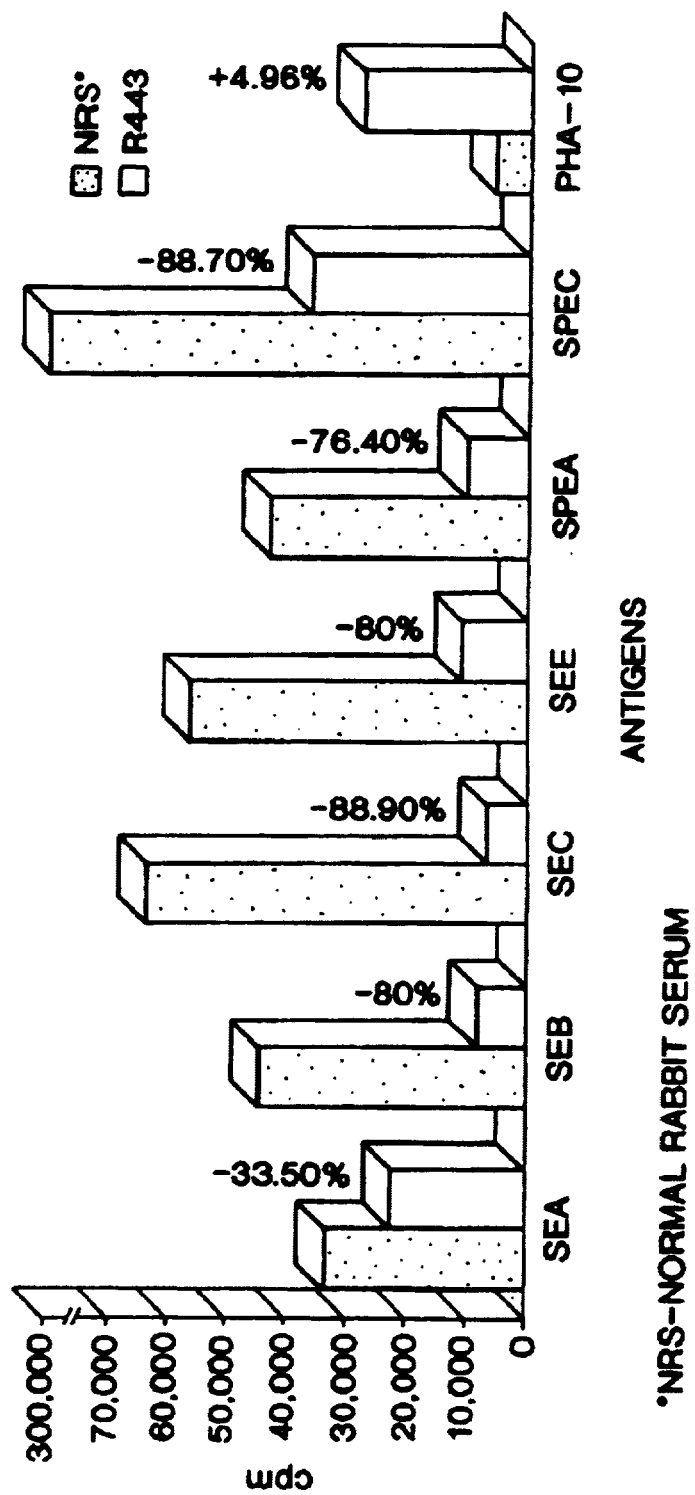
FIG. 6. Bar graphs of blastogenesis assays of human mononuclear cell populations stimulated by various toxins in the presence of normal rabbit serum and anti-peptide 6348 serum. Note the marked inhibition of SEB, SEC, SEE, SPEA and SPEC by the anti-peptide antibody. Less, but definite, inhibition of SEA by the anti-peptide antibody was also seen.

The percentage of inhibition, of toxin mediated blastogenesis, by AP6348 was assayed. Tritiated thymidine incorporation by human PBMC stimulated with staphylococcal and streptococcal pyrogenic toxins was significantly inhibited by the addition of AP6348 compared to normal rabbit serum (NRS) (FIG. 6). This suggests blastogenesis of PBMC in response to the toxins was inhibited by AP6348. The AP6348 serum did not affect the blastogenesis of human PBMC in response to PHA, suggesting a specific inhibition of toxin biologic activity.

In vivo Protection of Rabbits

We tested the ability of AP6348 serum to prevent severe toxic shock in rabbits challenged with SEB and NRS. Rabbits challenged intravenously with a mixture of SEB and NRS developed symptoms of severe toxic shock (Table 2). One rabbit receiving 50 µg/kg SEB with NRS, and two receiving 100 µg/kg of SEB with NRS, developed severe toxic shock and were declared moribund within 30 hrs. In contrast, two rabbits challenged with 50 ag/kg and 100 µg/kg SEB with AP6348 developed fever, but this returned to normal by 32 hours. No diarrhea or cardiopulmonary depression was observed. Rabbits were followed for a total of 5 days (data not shown) and appeared fully recovered.

TABLE 2

Passive Protection of Rabbits Challenged with SEB, SPEA and LPS

| Toxin | LPS | | Temperature° F. | | | | |
|---|---|---|---|---|---|---|---|
| µg/kg\Serum | µg/kg | Diarrhea | 0 hr | 4 hr | 24 hr | 32 hr | 48 hr |
| SEB | | | | | | | |
| ns$^f$\NRS | 5 | − | 100.4 | 102 | 101.4 | 101.2 | NT |
| 50\NRS | 5 | + | 101 | 104.4 | 102.8 | 96◊ | |
| 100\NRS | 5 | + | 102 | 104.6 | 103 | 97◊ | |
| 100\NRS | 5 | + | 101 | 104.5 | 102.6 | 97◊ | |
| 50\APS | 5 | − | 101.4 | 103.8 | 103 | 102 | 101 |
| 100\APS | 5 | − | 100.4 | 104.4 | 103 | 102 | 101 |

TABLE 2-continued

Passive Protection of Rabbits Challenged with SEB, SPEA and LPS

| Toxin | LPS | | Temperature° F. | | | | |
|---|---|---|---|---|---|---|---|
| μg/kg\Serum | μg/kg | Diarrhea | 0 hr | 4 hr | 24 hr | 32 hr | 48 hr |
| SPEA | | | | | | | |
| 50\NRS | 5 | + | 101 | 104.2 | NT ◊ | | |
| 100\NRS | 5 | + | 102 | 104.8 | NT ◊ | | |
| 50\APS | 5 | − | 102 | 104 | 103 | 102 | 102 |
| 100\APS | 5 | + | 101.6 | 104.4 | 104 | 100 | 97 ◊ | ns[f] = control rabbit given isotonic saline in place of SEB or SPEA
NRS = Normal rabbit serum
APS = Anti-peptide 6348 serum
◊ = animals were declared moribund
NT = not taken Discussion Our results demonstrate that antibodies rabbit antiserum generated to peptides representative of two regions with highly conserved amino acid sequences (AP6348) are capable of recognizing most of the staphylococcal enterotoxins and streptococcal pyrogenic exotoxins (e.g. SEA, SEB, SEC, SEE, SPEA, SPEC), as well as TSST-1, using Western blots. We expect that other, more sensitive assays, will result in the demonstration of binding of these antibodies to additional members, probably all members, of the staphylococcal and streptococcal pyrogenic toxin family.

Since recognition of the toxins by AP6348 was successful, we tested this serum for the ability to inhibit the biological effects of these pyrogenic toxins. AP6348 was capable of inhibiting in vitro blastogenesis of human PBMCs by many of the pyrogenic toxins (e.g., SEA, SEB, SEC, SEE, SPEA, and SPEC).

AP6348 was also able to provide passive in vivo protection of animals challenged with lethal doses of SEB and SPEA. These animals developed fever, however the fever returned to normal within 30 hours and remained normal. Rabbits appeared to be fully recovered within days of challenge.

In contrast, rabbits receiving similar doses of SEB and SPEA pre-incubated with NRS developed severe toxic shock as evidenced by high fevers, diarrhea, and cardiopulmonary distress. The illness progressed and these animals were declared moribund.

The therapeutic and biological implications of these observations are as follows: (i) antibodies prepared against this peptide may be administered during the early stages of toxic shock or septic shock irrespective of the toxin causing the symptoms and (ii) the peptide may be used as an immunogen to block the toxic effects of this family of superantigens.

EXAMPLE 2

Figure 7:
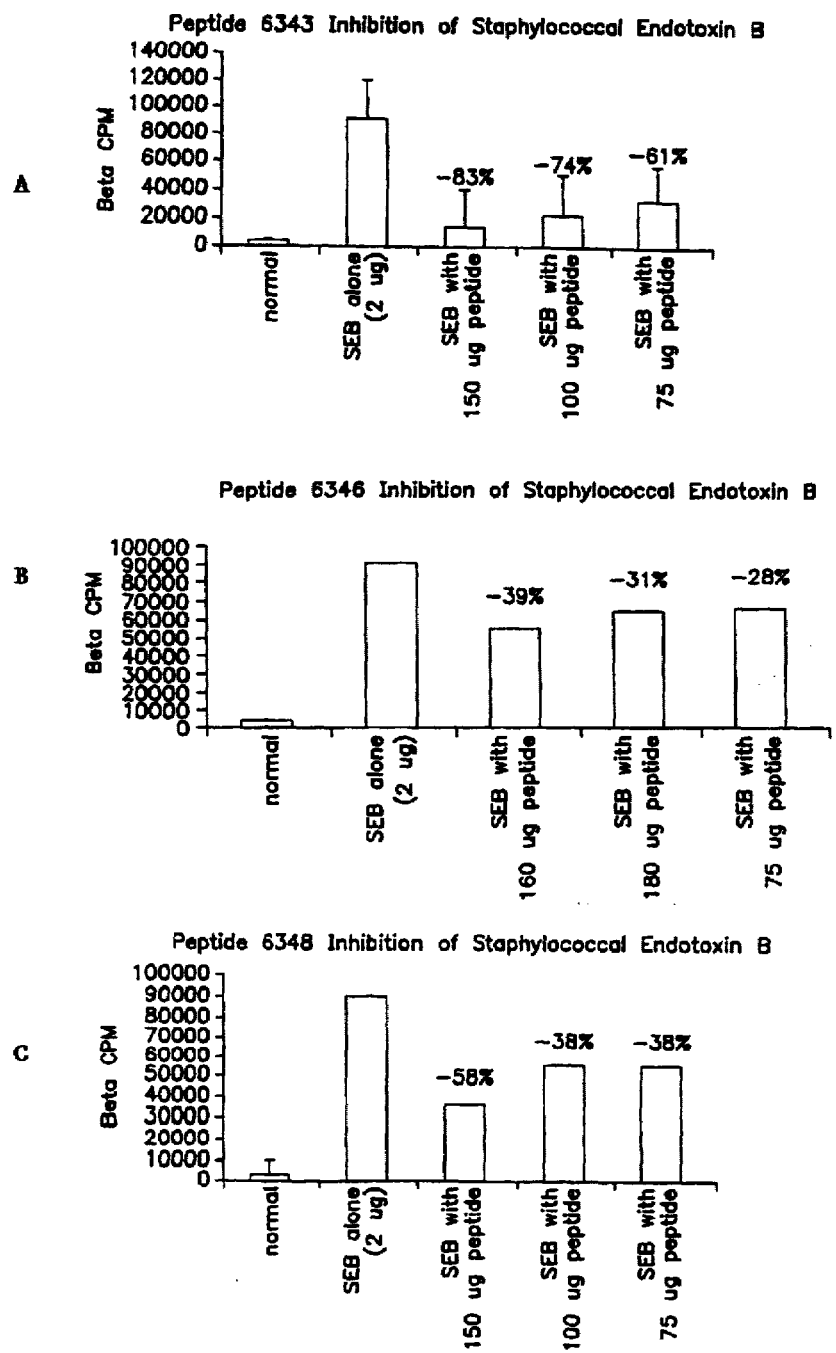
FIG. 7. Bar graphs of blastogenesis assays of human mononuclear cell populations stimulated by SEB in the presence of (A) peptide 6343 (i.e., CMYGGVTEHEGN, SEQ ID NO:3), (B) peptide 6346 (i.e., CGKKN-VTVQELDYKIRKYLVDNKKLYGC, SEQ ID NO: 6)) and (C) peptide 6348 (i.e., CMYGGVTEHEGNKKN-VTVQELDYKIRKYLVDNKKLYGC, SEQ ID NO:8).

PBMCs were isolated via Ficoll-Hypaque Solution. The appropriate concentration of nonpolymeric peptide and $2 \times 10^5$ cells in 200 μL of RPMI solution was plated in each well. The cells were incubated for one hour at 37 degrees Centigrade, with mild agitation every 15 minutes. After one hour, 2 μg of SEB was added in each well. The PBMCs were incubated for 72 hours and the results were measured via tritiated thymidine incorporation. The cells were collected and read on a beta counter. The results are shown in FIG. 7.

Note the dose-response inhibition of blastogenesis demonstrated in FIG. 7A. Peptide 6343 (i.e., CMYGGVTEGEGN, SEQ ID NO:3)(FIG. 7A) showed more inhibitory activity of SEB than peptide 6346 (i.e., CGKKNVTVQELDYKIRKY-LVDNKKLYGC, SEQ ID NO:6) (FIG. 7B) or peptide 6348 (i.e., CMYGGVTEHEGNKKNVTVQELDYKIRKY-LVDNKKLYGC, SEQ ID NO:8) (FIG. 7C).

EXAMPLE 3

Figure 8:
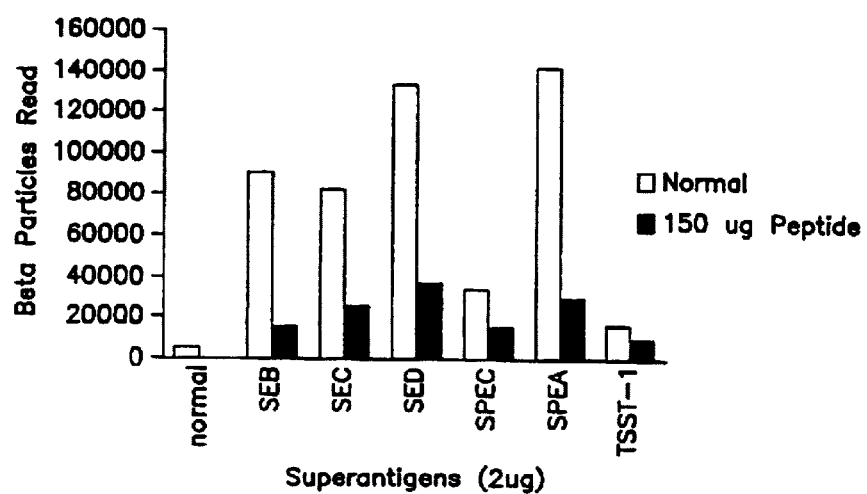
FIG. 8. Inhibition of SEB, SEC, SED, SPEC, SPEA and TSST-1 toxin blastogenesis of peripheral blood mononuclear cells (PBMC) by the 6343 peptide. $2 \times 10^5$ PBMC were stimulated with either 2 μg of the indicated toxin or a combination of 2 μg of the toxin with 150 μg of the 6343 peptide. These were incubated for 72 hours and the results were measured via tritiated thymidine incorporation. CPM represents counts per minute. Note that the single peptide (6343) inhibited all of the superantigens tested.
Figure 9:
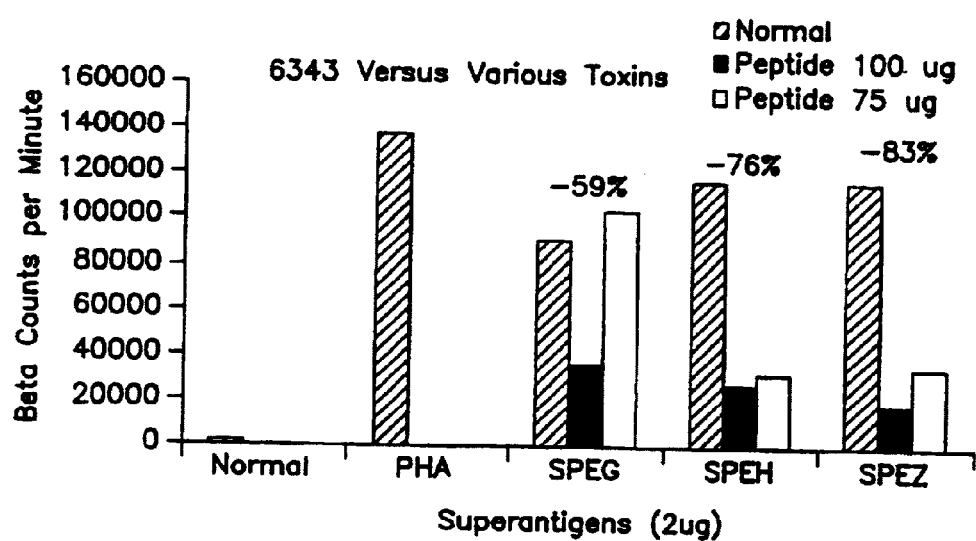
FIG. 9. Inhibition of SPEG, SPEH, and SPEZ toxin blastogenesis of peripheral blood mononuclear cells (PBMC) by the 6343 peptide. $2 \times 10^5$ PBMC were stimulated with either 2 μg of the indicated toxin or a combination of 2 μg of the toxin with the indicated amount of the 6343 peptide. These were incubated for 72 hours and the results were measured via tritiated thymidine incorporation. CPM represents counts per minute. Normal represents normal media. Note that the single peptide (6343) inhibited the superantigens SPEG, SPEH and SPEZ.
Figure 10:
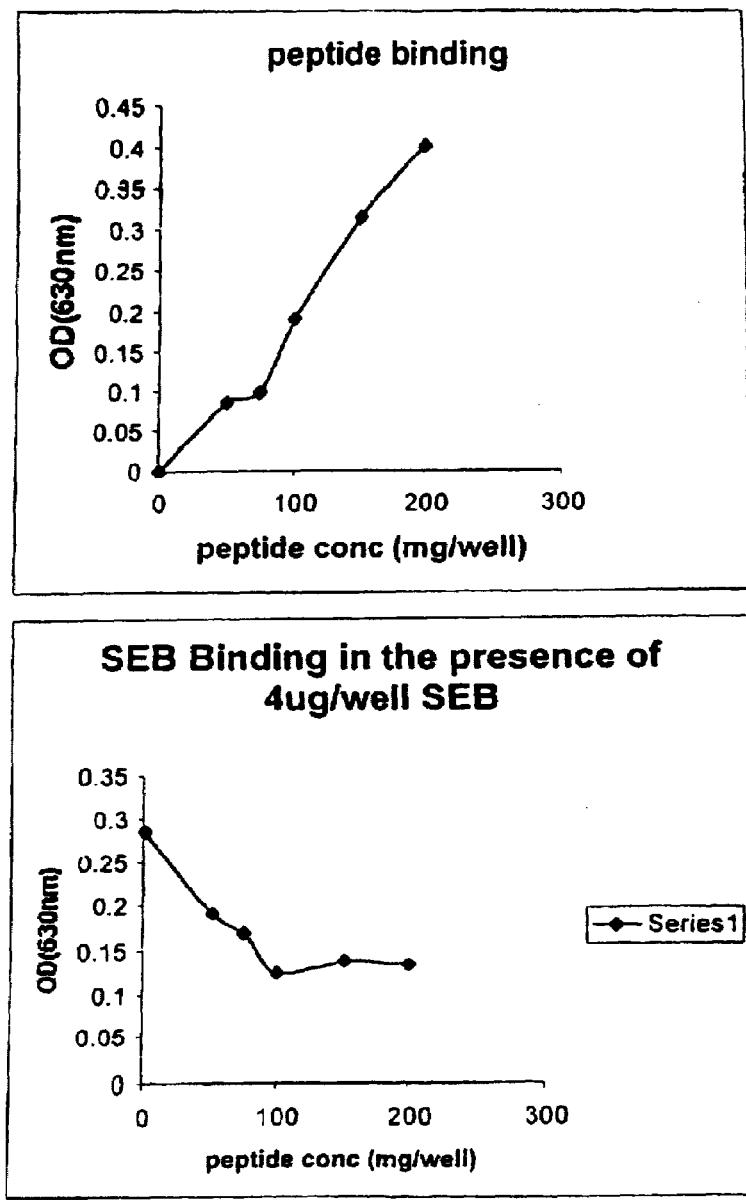
FIG. 10. (A). Binding of peptide 6343 to the MHC complex as measured by ELISA. (B). Inhibition of binding of SEB toxin biding by peptide 6343 as measured by decreased anti-SEB binding at increased concentrations of added peptide 6343.
Figure 11:
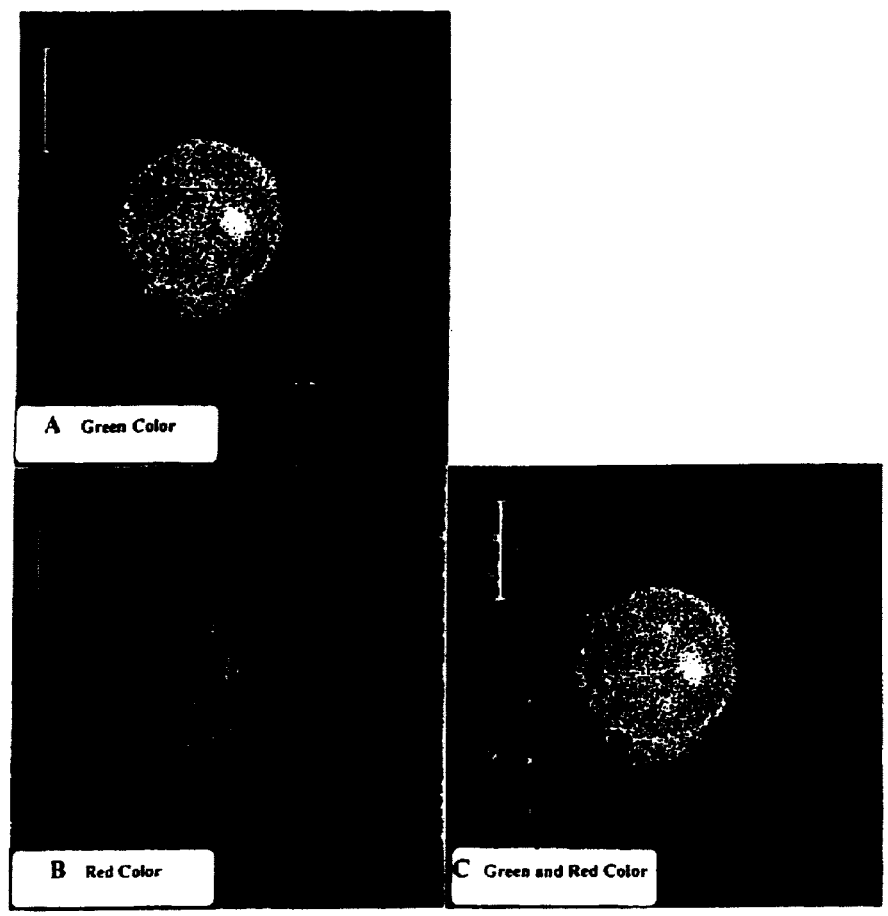
FIG. 11. Confocal microscope pictures. (A) Binding of peptide 6343 is indicated by the green color. (B) Binding of anti-MHC peptide is indicated by the red color. (C) Combined picture showing stippled pattern of red and green color. Binding of peptide 6343 is indicated by the green color and binding of anti-MHC peptide is indicated by the red color.

PBMCs were isolated via Ficoll-Hypaque Solution. 150 μg of nonpolymeric 6343 peptide (i.e., CMYG-GVTEGEGN, SEQ ID NO:3) and $2 \times 10^5$ cells in 200 μL of RPMI solution was plated in each well. The cells were incubated for one hour at 37 degrees Centigrade, with mild agitation every 15 minutes. After one hour, 2 μg of either SEB, SEC, SED, SPEC, SPEA, or TSST-1 was added to each well. The PBMCs were incubated for 72 hours and the results were measured via tritiated thymidine incorporation. The cells were collected and read on a beta counter. All experiments were run in triplicate. The results are shown in FIG. 8. Note that peptide 6343 inhibited blastogenesis of PBMCs by all of the superantigens tested.

EXAMPLE 4

Two-Hit Septic Shock Model

Figure 2:
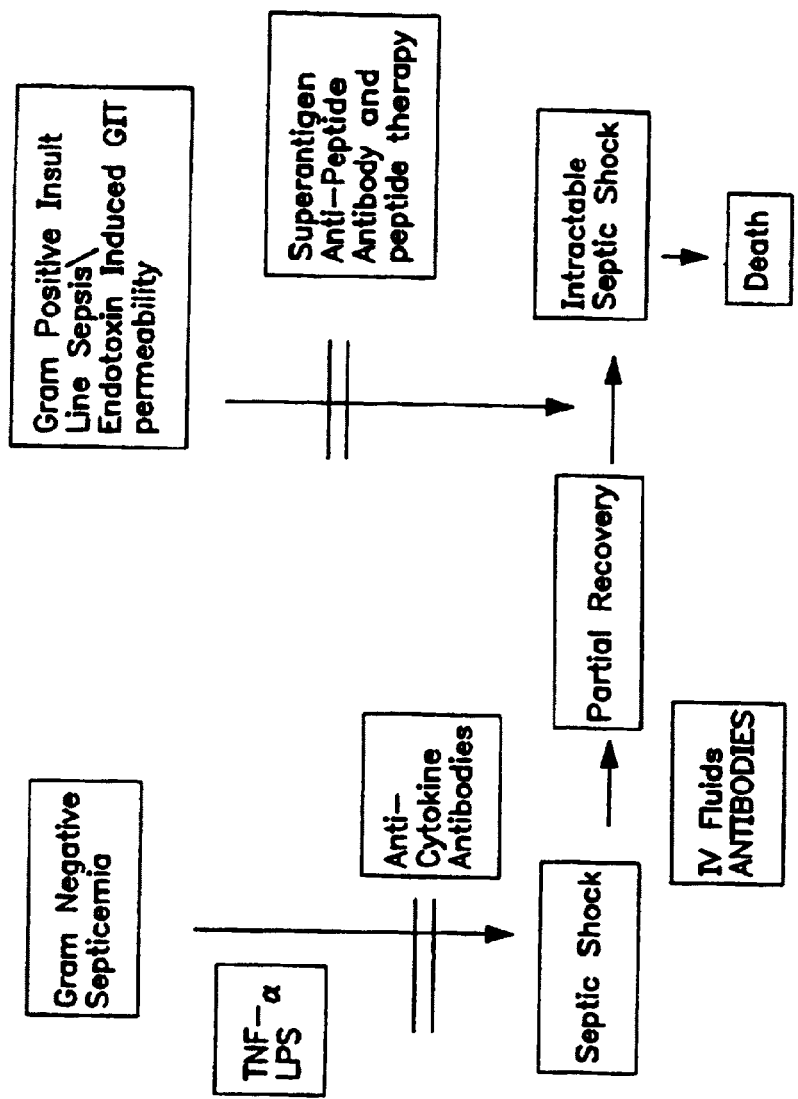
FIG. 2. Diagram of the "two hit" model of septic shock.

Based on the two hit septic shock hypothesis described in the background and FIG. 2 we have created a model of septic shock. While the amounts of either SPEA or SEB superantigens used in the rabbit model were relatively high, the amounts used in the mouse model were much lower due to D-galactosamine priming, size of animals and synergy between the toxins and LPS. BALB/c mice challenged intra-peritoneally after priming with D-galactosamine (20 mg/mouse) concurrently with LPS followed by SEB, showed that extremely small amounts of LPS and SEB were needed to effect lethality (46). The synergy between these two mediators of shock was extremely impressive and extended for at least an 18 hour period. We chose an 8 hour delay between the two toxins for our model. We established and optimized doses of toxin for SEA, SEB, SPEA, SPEC, and TSST-1 that would lead to 100% lethality. The doses of the various toxins are shown in Table 3.

TABLE 3

Doses of various toxins and LPS/D-galactosamine used in the lethal two hit septic shock model

| | SEA | SPEA | SEB | SPEC | TSST-1 |
|---|---|---|---|---|---|
| Toxin (μg) | 2.5 | 2.0 | 0.02 | 2.5 | 2.0 |
| LPS (μg) | 0.001 | 0.001 | 0.001 | 0.001 | 0.001 |
| D-galactosamine (mg) | 20 | 20 | 20 | 20 | 20 mg |

EXAMPLE 5

All mice were sensitized with 0.001 μg Lipopolysaccharide (LPS) and 20 mg of D-Galactosamine via intraperioneal injection. The results are shown in Table 4. After six hours, saline or 1.5 mg of the nonpolymeric peptide 6343 was administered to the experimental mice by subcutaneous injection. One hour later, the mice were injected again with either saline or 1.5 mg peptide (3.0 mg total). One hour later, all mice were challenged with 0.02 μg SEB, SPEA or TSST-1 (via intraperitoneal injection) and the mice were observed overnight. In this model, it has been observed that peptide 6343, given one and two hours before administration of the toxic dose of the indicated toxin, protected 5 out of 6 mice exposed to toxin SEB; 2 out of 2 mice exposed to the toxin SPEA and 2 out of two mice exposed to the toxin TSST-1.

TABLE 4

The Use of Peptide 6343 to Block the Superantigen Induction of Septic Shock in a Mouse Model

| Mice | Dose and Administration | Alive/Total SEB | Alive/Total SPEA | Alive/Total TSST-1 |
|---|---|---|---|---|
| Control | Saline subcutaneous injection | 0/6 (0%) | 0/2 (0%) | 0/2 (0%) |
| Peptide 6343 | 3.0 mg subcutaneous injection | 5/6 (83%) | 2/2 (100%) | 2/2 (100%) |

EXAMPLE 6

Two streptococcal antigens SEG and SEH have recently been synthesized and three new streptococcal exotoxins, i.e., SPEG, SPEH and SPEZ, have recently been described by Dr. Fraser and colleagues (61).

In order to determine whether 6343 peptide is capable of inhibiting the toxic effects of the streptococcal exotoxins SPEG, SPEH and SPEZ, experiments similar to those described above were conducted.

In a similar manner as above, PBMCs were isolated via Ficoll-Hypaque Solution. Either 0 µg, 75 µg, 100 µg or 150 µg of nonpolymeric 6343 peptide (i.e., CMYG-GVTEGEGN, SEQ ID NO:3) and $2\times10^5$ cells in 200 µL of RPMI solution was plated in each well. The cells were incubated for one hour at 37 degrees Centigrade, with mild agitation every 15 minutes. After one hour, 2 µg of the recombinant forms of either SPEG, SPEH, SPEZ, which were provided by Dr. Fraser of the University of Auckland, New Zealand, was added to each well. The PBMCs were incubated for 72 hours and the results were measured via tritiated thymidine incorporation. The cells were collected and read on a beta counter. The results are shown in FIG. 9. Note that peptide 6343 inhibited blastogenesis of PBMCs by the bacterial superantigens SPEG, SPEH and SPEZ.

EXAMPLE 7

To determine the nature of the inhibition of superantigen stimulation by the inhibitory peptides and antigens, purified MHC class II molecules (obtained from J. Strominger, Harvard University) were used in a competitive ELISA to determine binding to this molecule. The purified MHC were immobilized on a 96 well plate and 4 µg SEB was added. After appropriate washing a rabbit monoclonal anti-SEB antibody (Toxin Tech) was added to the ELISA followed by a calorimetric reagent. The plate was read on an ELISA plate reader. In similar experiments various concentrations of the peptide 6343 (i.e., Oig, 5 µg, 75 µg, 100 µg, or 150 µg) were added to the immobilized MHC before the addition of SEB. Binding of the peptide to the MHC was demonstrated by the decreased amount of SEB bound to the MHC, as indicated by a decreased amount of antibody binding measured by a decreased color reaction. The results are shown in FIG. 11. The results indicate that peptide 6343 binds very strongly to the MHC complex and is able to compete effectively for the site of SEB binding.

The binding of the peptide to the MHC complex of monocytes was supported by con-focal microscopy results of experiments using a method described in Ojcius et al. (68) using fluorinated peptides constructed for us by NEN Life-Sciences, antibodies directed against MHC class II proteins, and a phycoerythrin (PE) antibody directed to the anti-MHC antibody. Various doses of the peptide and various concentrations of the cells were titrated to achieve optimum binding of the peptide. Confocal microscope pictures (FIG. 11) show similar patterns of binding for anti-MHC antibodies and for the flourinated peptides, supporting the determination that the peptide binds to the cells' MHC complex.

Discussion

In the experiments described herein, the dose of peptide 6343 used directly for the prevention of toxic and septic shock was 3 mgs per mouse. Thus, the direct use of peptides in septic or toxic shock would be expected to involve doses in the range of several grams for the acute treatment of shock in humans. Peptide 6343, possibly because of its small size, does not induce detectable antibodies in rabbits and mice, yet it still has all the therapeutic properties described for the anti-peptide antibodies. Therefore, if desired, it is expected that the peptide can be used repeatedly in the same individual without raising anti-peptide antibodies.

REFERENCES

1. Bergdoll, M. S. 1985. The staphylococcal enterotoxins-an update., 247–254. In J. Jeljaszewicz (ed.). The staphylococci. Gustav Fischer Verlag, New York, N.Y.
2. Blomster-Hautamaa, D. A., B. N. Kreiswirth, J. S. Kornblum, R. P. Novick and P. M. Schlievert. 1986. The nucleotide and partial amino acid sequence of toxic shock syndrome toxin-1. Journal of Biological Chemistry. 261: 15783–15786.
3. Choi, Y., B. Kotzin, L. Herron, J. Callahan, P. Marrack and J. Kappler. 1989. Interaction of *staphylococcus aureus* toxin superantigens with human T cells. Proc. Natl. Acad. Sci. USA. 86:8941.
4. Fleischer, B. and H. Schrezenmeier. 1988. T cell stimulation by staphylococcal enterotoxins. Clonally variable response and requirement for major histocompatibility complex class II molecules on accessory or target cells. Journal of Experimental Medicine. 167:1697.
5. Goshorn, S. C. and P. M. Schlievert. 1988. Nucleotide sequence of streptococcal exotoxin type C. Infect. Immun. 56:2518–2520.
6. Grossman, D., M. Van, J. A. Mollick, S. K. Highlander and R. R. Rich. 1991. Mutation of the disulfide loop in staphylococcal enterotoxin A. Consequences for T cell recognition. J. Immunol. 147:3274–3281.
7. Hartwig, U. F. and B. Fleisher. 1993. Mutations affecting MHC class II binding of the superantigen streptococcal erythrogenic toxin A. International Immunology. 5:869–875.
8. Hauser, A. R., D. L. Stevens, E. L. Kaplan and P. M. Schlievert. 1991. Molecular analysis of pyrogenic exotoxins from *streptococcus pyogenes* isolates associated with toxic shock-like syndrome. Journal of Clinical Microbiology. 29:1562–1567.
9. Hensler, T., M. Köller, C. Geoffroy, J. E. Alouf and W. König. 1993. *Staphylococcus aureus* toxic shock syndrome toxin 1 and *streptococcus pyogenes* erythrogenic toxin A modulate inflammatory mediator release from human neutrophils. Infect. Immun. 61:1055–1061.
10. Houghten, R. A. 1985. General method for the is rapid solid phase synthesis of large numbers of peptides: specificity of antigen-antibody interactions at the level of individual amino acids. Proc. Natl. Acad. Sci. USA. 82:5131–5135.
11. Hynes, W. L., C. R. Weeks, J. J. Iandolo and J. J. Ferretti. 1987. Immunologic cross-reactivity of type A streptococcal exotoxin (erythrogenic toxin) and staphylococcal enterotoxins B and Cl. Infect. Immun. 55:837–840.
12. Janeway, C. A. J., J. Yagi, P. J. Conrad, M. E. Katz, B. Jones, S. Vroegop and S. Buxser. 1989. T-cell responses to Mls and to bacterial proteins that mimic its behavior. Immunology Reviews. 107:61.
13. Johnson, L. P., J. J. L'Italien and P. M. Schlievert. 1986. Streptococcal pyrogenic exotoxin type A (scarlet fever toxin) is related to *staphylococcus aureus* enterotoxin B. Molecular and General Genetics. 203:354–356.
14. Kappler, J., B. L. Kotzin, L. Herron, E. W. Gelfand, R. D. Bigler, A. Boylston, S. Carrell, D. N. Posnett, Y. Choi and P. Marrack. 1989. VP-specific stimulation of human T-cells by staphylococcal toxins. Science. 248:705.
15. Kappler, J. W., A. Herman, J. Clements and P. Marrack. 1992. Mutations defining functional regions of the superantigen staphylococcal enterotoxin B. Journal of Experimental Medicine. 175:387–396.
16. Laemmli, U. K. 1970. Cleavage of structural proteins during the assembly of the head of bacteriophage T4. Nature. 227:680.
17. Leonard, B. A. and P. M. Schlievert. 1992. Immune cell lethality induced by streptococcal pyrogenic exotoxin A and endotoxin. Infect. Immun. 60:3747–3755.
18. Marrack, P., M. Blackman, E. Kushnir and J. Kappler. 1990. The toxicity of staphylococcal enterotoxin B in mice is mediated by T cells. Journal of Experimental Medicine. 171:455.
19. Marrack, P. and J. Kappler. 1990. The staphylococcal enterotoxins and their relatives. Science. 248:705–711.
20. Merrifield, R. B. 1963. Solid-phase peptide synthesis I. The synthesis of a tetrapeptide. J. Am. Chem. Soc. 85:2149–2154.
21. Musser, J. M., A. R. Hauser, M. H. Kim, P. M. Schlievert, K. Nelson and R. K. Selander. 1991. *Streptococcus pyogenes* causing toxic-shock-like syndrome and other invasive diseases: clonal diversity and pyrogenic exotoxin expression. Proceedings of the National Academy of Sciences of the United States of America. 88:2668–2672.
22. Read, S. E., H. F. M. Reid, V. A. Fischetti, T. Poon-King, R. Ramkissoon, M. McDowell and J. B. Zabriskie. 1986. Serial studies on the cellular immune response to streptococcal antigens in acute and convalescent rheumatic fever patients in Trinidad. Journal of Clinical Immunology. 6:433–441.
23. Reda, K. B., V. Kapur, J. A. Mollick, J. G. Lamphear, J. M. Musser and R. R. Rich. 1994. Molecular characterization and phylogenetic distribution of the streptococcal superantigen gene (ssa) from *streptococcus pyogenes*. Infect. Immun. 62:1867–1874.
24. Ren, K., J. D. Bannan, V. Pancholi, A. L. Cheung, J. C. Robbins, V. A. Fischetti and J. B. Zabriskie. 1994. Characterization and biological properties of a new staphylococcal exotoxin. Journal of Experimental Medicine. 180:1675–1683.
25. Smith, R. J., P. M. Schlievert, I. M. Himelright and L. M. Baddour. 1994. Dual infections with *staphylococcus aureus* and *streptococcus pyogenes* causing toxic shock syndrome. Possible synergistic effects of toxic shock syndrome toxin 1 and streptococcal pyrogenic exotoxin C. Diagnostic Microbiology & Infectious Disease. 19:245–247.
26. Spero, L., B. Morlock and J. Metzger. 1978. On the cross-reactivity of staphylococcal enterotoxins A, B, and C. J. Immunol. 120:86–89.
27. Spero, L. and B. A. Morlock. 1978. Biological activities of the peptides of staphylococcal enterotoxin C formed by limited tryptic hydrolysis. Journal of Biological Chemistry. 253:8787–8791.
28. Spero, L. and B. A. Morlock. 1979. Cross-reactions between tryptic polypeptides of staphylococcal enterotoxins B and C. J. Immunol. 122:1285–1289.
29. Stelma, G. N., Jr. and M. S. Bergdoll. 1982. Inactivation of staphylococcal enterotoxin A by chemical modification. Biochemical and Biophysical Research Communications. 105:121–126.
30. Stevens, D. L., M. H. Tanner, J. Winship, R. Swarts, K. M. Ries, P. M. Schlievert and E. Kaplan. 1989. Severe group A streptococcal infections associated with a toxic shock-like syndrome and scarlet fever toxin A. The New England Journal of Medicine. 321:1–7.
31. Sugiyama, H., E. M. J. McKissic, M. S. Bergdoll and B. Heller. 1964. Enhancement of bacterial endotoxin lethality by staphylococcal enterotoxin. J. Infect. Dis. 114:111–118.
32. Swaminathan, S., W. Furey, J. Pletcher and M. Sax. 1992. Crystal structure of staphylococcal enterotoxin B, a superantigen. Nature. 359:801–806.
33. Towbin, H., T. Staehlin and J. Gordon. 1979. Electrophoretic transfer of proteins from polyacrylamide gels to nitrocellulose sheets. Procedure and some applications. Proceedings of the National Academy of Sciences, USA. 76:4350.
34. Van den Bussche, R. A., J. D. Lyon and G. A. Bohac. 1993. Molecular evolution of the staphylococcal and streptococcal pyrogenic toxin gene family. Molecular Phylogenetics and Evolution. 2:281–292.
35. Weeks, C. R. and J. J. Ferretti. 1986. Nucleotide sequence of the type A streptococcal exotoxin (erythrogenic toxin) gene from *streptococcus pyogenes* bacteriophage T12. Infect. Immun. 52:144–150.
36. White, J., A. Herman, A. M. Pullen, R. Kubo, J. W. Kappler and P. Marrack. 1989. The V beta-specific superantigen staphylococcal enterotoxin B: stimulation of mature T cells and clonal deletion in neonatal mice. Cell. 56:27–35.
37. Patarroyo, M. E., R. Amador, P. Clavijo, A. Moreno, F. Guzman, P. Romero, R. Tascon, A. Franco, L. A. Murillo, G. Ponton and G. Trujillo. 1988. A synthetic vaccine protects humans against challenge with *Plasmodium falciparum* malaria. Nature. 332:158–161.
38. Lopez, M. C., Y. Silva, M. C. Thomas, A. Garcia, M. J. Faus, P. Alonso, F. Martinez, G. Del Real and C. Alonso. 1994. Characterization of SPf(66)$_n$: a chimeric molecule used as a malaria vaccine. Vaccine. 12:585–591.
39. Rodriguez, R., A. Moreno, F. Guzman, M. Calvo and M. E. Patarroyo. 1990. Studies in owl monkeys leading to the development of a synthetic vaccine against the asexual blood stages of *Plasmodium falciparum*. Am. J. Trop. Med. Hyg. 43:339–354.
40. Hoffman, M. L., L. M. Jablonski, K. K. Crum, S. P. Hackett, Y.-I. Chi, C. V. Stauffacher, D. L. Stevens and G. A. Bohach. 1994. Predictions of T-cell receptor and Major Histocompatibility Complex-binding sites on staphylococcal enterotoxin Cl. Infection and Immunity. 62:3396–3407.
41. Acharya, K. R., E. F. Passalacqua, E. Y. Jones, K. Harlos, D. I. Stuart, R. D. Brehm and H. S. Tranter (1994). "Structural basis of superantigen action inferred from crystal structure of toxic-shock syndrome toxin-1." Nature 367: 94–97.
42. DELETED
43. Bannan, J. D., F. Mingo, A. Viteri and J. B. Zabriskie (1997). "Neutralization of streptococcal pyrogenic exotoxins and staphylococcal enterotoxins by antisera to synthetic peptides representing conserved amino acid motifs." Adv Exp Med Biol 418: 903–907.
44. Bartus, R. T., M. A. Tracy, D. F. Emerich and S. E. Zale (1998). "Sustained delivery of proteins for novel therapeutic agents." Science 281(5380): 1161–2.
45. Baumgartner, J. D. (1990). "Monocolonal anti-endotoxin antibodies for the treatment of gram-negative bacteremia and septic shock." Eur J Clin Microbiol Infect Dis 9(10): 711–6.
46. Blank, C., A. Luz, S. Bendigs, A. Erdmann, H. Wagner and K. Heeg (1997). "Superantigens and endotoxin synergize in the induction of lethal shock." Eur J Immunol 27(4): 825–833.
47. Bohach, G. A., C. J. Hovde, J. P. Handley and P. M. Schlievert (1988). "Cross-Neutralizaton of staphylococcal and streptococcal pyrogenic toxins by monoclonal and polyclonal antibodies." Infect Immun 56(2): 400–404.
48. Chorev, M. and M. Goodman (1995). "Recent developments in retro peptides and proteins—an ongoing topochemical exploration." Trends Biotechnol 13(10): 438–45.
49. Cohen, L., B. David and J. M. Cavaillon (1991). "Interleukin-3 enhances cytokine production by LSP-stimulated macrophages." Immunol Lett 28(2): 121–6.
50. Edwin, C., S. R. Tatini and S. K. Maheswaran (1986). "Specificity and cross-reactivity of staphylococcal enterotoxin A monoclonal antibodies with enterotoxins B, Cl, D, and E." App Environ Micro 52(6): 1253–7.
51. Fleischer, B., D. Gerlach, A. Fuhrmann and K. H. Schmidt (1995). "Superantigens and pseudosuperantigens of gram-positive cocci." Med Micro Immunol 184(1): 1–8.
52. Glauser, M. P. (1996). "The inflammatory cytokines. New developments in the pathophysiology and treatment of septic shock." Drugs 52 Suppl 2: 9–17.
53. Griggs, N. D., C. H. Pontzer, M. A. Jarpe and H. M. Johnson (1992). "Mapping of multiple binding domains of the superantigen staphylococcal enterotoxin A for HLA." J Immunol 148(8): 2516–2521.
54. Grossman, D., R. G. Cook, J. T. Sparrow, J. A. Mollick and R. R. Rich (1990). "Dissociatioin of the stimulatory activities of staphylococcal enterotoxins for T cells and monocytes." J Exp Med 172(6): 1831–1841.
55. Hoffmann, M. L., L. M. Jablonski, K. K. Crum, S. P. Hackett, Y.-I. Chi, C. V. Stauffacher, D. L. Stevens and G. A. Bohach (1994). "Predictions of T-cell receptor and major histocompatibility complex-binding sites on staphylococcal enterotoxin Cl." Infect Immun 62: 3396–3407.
56. Howe, L. M. (1998). "Treatment of endotoxic shock: glucocorticoids, lazaroids, nonsteroidals, others." Vet Clin North Am Small Anim Pract 28(2): 249–67.
57. Jeong, B., Y. H. Bae, D. S. Lee and S. W. Kim (1997). "Biodegradable block copolymers as injectable drug-delivery systems." Nature 388(6645): 860–2.
58. Jett, M., R. Neill, C. Welch, T. Boyle, E. Bernton, D. Hoover, G. Lowell, R. E. Hunt, S. Chatterjee and P. Gemski (1994). "Identification of staphylococcal enterotoxin B sequences important for induction of lymphocyte proliferation by using synthetic peptide fragments of the toxin.” Infect Imun 62(8): 3408–3415.
59. Mollick, J. A., R. L. McMasters, D. Grossman and R. R. Rich (1993). “Localization of site on bacterial superantigens that determines T cell receptor beta chain specificity.” J Exp Med 177(2): 282–293.
60. Pontzer, C. H., N. D. Griggs and H. M. Johnson (1993). “Agonist properties of a microbial superantigen peptide.” Biochem Biophys Res Commun 193(3): 1191–1197.
61. Proft, T., S. L. Moffat, C. J. Berkahn and J. D. Fraser (1999). “Identification and Characterization of Novel Superantigens from *Streptococcus pyogenes*.” J Exp Med. 189(1):89–102.
62. Schlievert, P. M., G. A. Bohach, D. H. Ohlendorf, C. V. Stauffacher, D. Y. Leung, D. L. Murray, C. A. Earhart, L. M. Jablonski, M. L. Hoffmann and Y. I. Chi (1995). “Molecular structure of *staphylococcus* and *streptococcus* superantigens.” J Clin Immunol 15(69supppl.)): 4–10s.
63. Schoenberg, M. H., M. Weiss and P. Radermacher (1998). “Outcome of patients with sepsis and septic shock after ICU treatment.” Langenbecks Arch Surg 383(1): 44–8.
64. Wang, M. H., H. D. Flad, W. Feist, J. Musehold, S. Kusumoto, H. Brade, J. Gerdes, H. T. Rietschel and A. J. Ulmer (1992). “Inhibition of endotoxin or lipid A-induced tumor necrosis factor production by synthetic lipid A partial structures in human peripheral blood mononuclear cells.” Lymphokine Cytokine Res 11(1): 23–31.
65. Warren, J. R., L. Spero and J. F. Metzger (1974). “Stabilization of native structure by the closed disulfide loop of staphylococcal enterotoxin B.” Bioch Biophys Acta 359: 351–363.
66. Weiss, K. A. and M. Layerdiere (1997). “Group A *Streptococcus* invasive infections: a review.” Can J Surg 40(1): 18–25.
67. Woodley, J. F. (1994). “Enzymatic barriers for GI peptide and protein delivery.” Crit Rev Ther Drug Carrier Syst 11(2–3): 61–95.
68. Ojcius, D. M., F. Niedergang, A. Subtil, R. Hellio, and A. Dautry-Varsat (1996). “Immunology and the confocal microscope.” Research in Immunology 147(3):175–188.
69. Soos, J M, Johnson H M: Multiple binding sites on the superantigen, staphylococcal enterotoxin B, imparts versatility in binding to MHC class II molecules. Biochem biophys Res commun 201:596–602, 1994.
70. Yagi J, Rath S, Janeway Calif., Jr: Control of T cell responses to staphylococcal enterotoxins by stimulator cell MHC class II polymorphism. J Immunol 147:13998–11405,1991.
71. Muller-Alouf H, Alouf J E, Gerlach D, et al: Human pro- and anti-inflammaotry cytokine patterns induced by *Streptococcus pyogenes* erythrogenic (pyrogenic) exotoxin A and C superantigens. Infect Immun 64:1450–1453, 1996.
72. Leung D Y, Travers J B, Giorno R, et al: Evidence for a streptococcal superantigen-driven process in acute guttate psoriasis. J Clin Invest 96:2106–2112, 1995.
73. Muller-Alouf H, Alouf J E, Gerlach D, et al: Comparative study of cytokine release by human peripheral blood mononuclear cells stimulated with *Streptococcus pyogenes* superantigenic erythrogenic toxins, heat killed streptococci, and lipopolysaccharide. Infect Immun 62:4915–4921, 1994.

74. Blankson J N, Morse S S: The CD28/B7 pathway cosimulates the response of primary murine T cells to superantigens as well as to conventional antigens. Cell Immunol 157:306–312, 1994.
75. Fleischer B, Schrezenmeier H: T cell stimulation by staphylococcal enterotoxins. Clonally variable response and requirement for major histocompatibility complex class II molecules on accessory or target cells. J Exp Med 167:1697, 1988.
76. Krakauer T: Cell adhesion molecules are co-receptors for staphylococcal enterotoxin B-induced T-cell activation and cytokine production. Immunol Lett 39:121–125, 1994.
77. van Seventer Ga., Newman W, Shimizu Y, et al: Analysis of T cell stimulation by superantigen plus major histocompatibility complex class II molecules or by CD3 monoclonal antibody: Costimulation by purified adhesion ligands VCAM-1 ICAM-1 but not ELAM-1. J Exp Med 174:901–913, 1991.
78. Chapes S K, Beharka A A, Hart M E, et al: Differential RNA regulation by staphylococcal enterotoxins A and B in murine macrophages. J Leukoc Biol 55:523–529, 1994.
79. Hackett S P, Stevens D L: Superantigens associated with staphylococcal and streptococcal toxic shock syndrome are potent inducers of tumor necrosis factor beta synthesis. J Infect Dis 168:232–235, 1993.
80. Imanishi K, Akatsuka H, Inada K, et al: IFN-gamma-stimulated human vascular endothelial cells function as accessory cells for superantigen-induced TNF production in human T-cells. Int Arch Allergy Immunol 106:163–165, 1995.
81. Blank C, Luz A, Bendigs S, et al: superantigens and endotoxin synergize in the induction of lethal shock. Eur J Immunol 27:825–833, 1997
82. Leonard B A, Schlievert P M: Immune cell lethality induced by streptococcal pyrogenic exotoxin A and endotoxin. Infect Immun 60:3747–3755, 1992.
83. Sugiyama H, McKissic EMJ, Bergdoll M S, et al: Enhancement of bacterial endotoxin lethality by staphylococcal enterotoxin. J Infect Dis 114:111–118, 1964.
84. Hensler T, Köller M, Geoffroy C, et al: *Staphylococcus aureus* toxic shock syndrome toxin 1 and *Streptococcus pyogenes* erythrogenic toxin A modulate inflammatory mediator release from human neutrophils. Infect Immun 61:1055–1061, 1993.
85. Smith R J, Schlievert P M, Himelright I M, et al: Dual infections with *Staphylococcus aureus* and *Streptococcus pyogenes* causing toxic shock syndrome. Possible synergistic effects of toxic shock syndrome toxin 1 and streptococcal pyrogenic exotoxin C. Diagn Microbiol Infect Dis 19:245–247, 1994.
86. Brocke S, Gaur A, Piercy C, et al: Induction of relapsing paralysis in experimental autoimmune encephalomyelitis by bacterial superantigen. Nature 365:642–644, 1993.
87. Kotzin B L, Leung D Y, Kappler J, et al: Superantigens and their potential role in human disease. Adv Immunol 54:99–166, 1993.
88. Li S, Quayle A J, Thoen J E, et al: Superantigen-mediated proliferation and cytotoxicity of T cells isolated from the inflammatory tissues and peripheral blood of arthritis patients. Clin Immunol Immunopathol 79:278–287, 1996.
89. Schiffenbauer J, Johnson H M, Butfiloski E J, et al: Staphylococcal enterotoxins can reactivate experimental allergic encephalomyelitis. Proc Natl Acad Sci USA 90:8543–8546, 1993.
90. Schleivert P M: Role of superantigens in human disease. J Infect Dis 167:997–1002, 1993.
91. Schwab J, Brown R, Anderle S, et al: Superantigen can reactivate baacterial cell wall-induced arthritis. J Immunol 150:4151–4159, 1993.
92. Astiz M, Saha D, Lustbader D, et al: Monocyte response to bacterial toxins, expression of cell surface receptors, and release of anti-inflammatory cytokines during sepsis. J Lab Clin Med 128:594–600, 1996.
93. Schleivert P M, Bohach Ga., Ohlendorf D H, et al: Molecular structure of *staphylococcus* and *streptococcus* superantigens. J Clin Immunol 15:4s$^{-10}$s, 1995.
94. Bannan J, Visvanathan K, and Zabriskie J B. "Structure and function of streptococcal and staphylococcal superantigens in Septic Shock," Infectious Disease Clinics of North America 13(2):387–396, 1999.
95. Senderoff R I, Kontor K M, Kreilgaard L, Chang J J, Patel S, Krakover J, Heffernan J K, Snell L B, Rosenberg G B. Consideration of conformational transitions and racemization during process development of recombinant glucagon-like peptide-1. Journal of Pharmaceutical Sciences. 87(2):183–9, 1998
96. Rangel-Frausto M S, Pittet D, Costigan M, Hwang T, Davis C S, Wenzel R P. The natural history of the systemic inflammatory response syndrome (SIRS). A prospective study. JAMA 273(2):117–23, 1995 Every reference cited hereinbefore is hereby incorporated by reference in its entirety.

Modifications of the above described modes for carrying out the invention that are obvious to those of skill in the fields of immunology, protein chemistry, microbiology, medicine, and related fields are intended to be within the scope of the following claims.

The data suggest a theory for a possible mechanism of action which is discussed in the application. However, the application describes how to make and use the invention. This description is not dependent upon theory and, accordingly, the claims are not bound by theory.

The following table shows the correspondence between peptides in FIG. 3 and their sequence identification numbers:

TABLE 5

Correspondence between Sequence Identification Numbers and Peptides in FIG. 3

| FIG. 3 | | | Sequence ID Nos. |
|---|---|---|---|
| Region 1 | | | |
| PEP | | CMYGGVTEHEGN | SEQ ID NO:3 |
| SEA | 130 | CMYGGVTLHDNN 141 | SEQ ID NO:9 |
| SEB | 140 | CMYGGVTEHNGN 151 | SEQ ID NO:10 |
| SEC | 137 | CMYGGITKHEGN 148 | SEQ ID NO:11 |
| SED | 131 | CTYGGVTPHEGN 142 | SEQ ID NO:12 |
| SEE | 130 | CMYGGVTLHDNN 141 | SEQ ID NO:13 |
| SEH | 116 | CLYGGITL.NSE 126 | SEQ ID NO:14 |
| SPEA | 128 | CIYGGVTNHEGN 139 | SEQ ID NO:15 |
| SPEC | 112 | YIYGGITPAQNN 123 | SEQ ID NO:16 |
| SSA | 134 | CMYGGVTEHHRN 145 | SEQ ID NO:17 |
| Region 2 | | | |
| PEP | | KKNVTVQELDYKIRKYLVDNKKLY | SEQ ID NO:4 |
| SEA | 171 | KKNVTVQELDLQARRYLQEKYNLY 194 | SEQ ID NO:18 |
| SEB | 179 | KKKVTAQELDYLTRHYLVKNKKLY 202 | SEQ ID NO:19 |
| SEC | 178 | KKSVTAQELDIKARNFLINKKNLY 201 | SEQ ID NO:20 |
| SED | 172 | KKNVTVQELDAQARRYLQKDLKLY 195 | SEQ ID NO:21 |
| SEE | 171 | KKEVTVQELDLQARHYLHGKFGLY 194 | SEQ ID NO:22 |
| SEH | 151 | KKNVTLQELDIKIRKILSDKYKIY 174 | SEQ ID NO:23 |

TABLE 5-continued

Correspondence between Sequence
Identification Numbers and Peptides in FIG. 3

| FIG. 3 | | Sequence ID Nos. |
|---|---|---|
| SPEA | 167 KKMVTAQELDYKVRKYLTDNKQLY 190 | SEQ ID NO:24 |
| SPEC | 151 KDIVTFQEIDFKIRKLYMDNYKIY 174 | SEQ ID NO:25 |
| SSA | 174 KKQVTVQELDCKTRKILVSRKNLY 197 | SEQ ID NO:26 |
| TSST1 | 161 KKQLAISTLDFEIRHQLTQIHGLY 184 | SEQ ID NO:27 |

---

We claim:

1. A non-toxic, purified peptide consisting of consecutive 15 amino acids having an amino acid sequence set forth in $X_{25}X_{26}YGGX_1TX_2X_3X_4X_5N$ wherein $X_1$ is V, $X_2$ is L, $X_3$ is H, $X_4$ is E, $X_5$ is G, $X_{25}$ is C, and $X_{26}$ is M (SEQ ID NO:34 CMY

SEQUENCE LISTING

<160> NUMBER OF SEQ ID NOS: 80

<210> SEQ ID NO 1
<211> LENGTH: 10
<212> TYPE: PRT
<213> ORGANISM: Artificial Sequence
<220> FEATURE:
<221> NAME/KEY: UNSURE
<222> LOCATION: (4)
<223> OTHER INFORMATION: XAA may be L, I or V
<221> NAME/KEY: UNSURE
<222> LOCATION: (6)..(9)
<223> OTHER INFORMATION: XAA may be any amino acid
<223> OTHER INFORMATION: Description of Artificial Sequence: Consensus
      Sequence derived from staphylococcal and
      streptococcal toxins

<400> SEQUENCE: 1

Tyr Gly Gly Xaa Thr Xaa Xaa Xaa Xaa Asn
 1               5                   10

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence:Consensus
      sequence derived from staphylococcal and
      streptococcal toxins
<221> NAME/KEY: UNSURE
<222> LOCATION: (11)..(13)
<223> OTHER INFORMATION: XAA may be any amino acid
<221> NAME/KEY: UNSURE
<222> LOCATION: (15)..(16)
<223> OTHER INFORMATION: XAA may be any amino acid
<221> NAME/KEY: UNSURE
<222> LOCATION: (2)..(3)
<223> OTHER INFORMATION: XAA may be any amino acid
<221> NAME/KEY: UNSURE
<222> LOCATION: (4)
<223> OTHER INFORMATION: XAA may be L, I or V
<221> NAME/KEY: UNSURE
<222> LOCATION: (5)..(8)
<223> OTHER INFORMATION: XAA may be any amino acid
<221> NAME/KEY: UNSURE
<222> LOCATION: (9)
<223> OTHER INFORMATION: XAA may be L, I or V
<221> NAME/KEY: UNSURE
<222> LOCATION: (18)..(22)
<223> OTHER INFORMATION: XAA may be any amino acid
<221> NAME/KEY: UNSURE
<222> LOCATION: (23)
<223> OTHER INFORMATION: XAA may be L, I or V

```
<400> SEQUENCE: 2

Lys Xaa Xaa Xaa Xaa Xaa Xaa Xaa Asp Xaa Xaa Xaa Arg Xaa Xaa
 1               5

```
<213> ORGANISM: Artificial Sequence
<220> FEATURE:
<223> OTHER INFORMATION: Description of Artificial Sequence:Consensus
      sequence derived from staphylococcal and
      streptococcal toxins

<400> SEQUENCE: 7

Cys Met Tyr Gly Gly Val Thr Glu His Glu Gly Asn Lys Lys Asn Val
 1               5                  10                  15

Thr Val Gln Glu Leu Asp Tyr Lys Ile Arg Lys Tyr Leu Val Asp Asn
            20                  25                  30

Lys Lys Leu Tyr
        35

<210> SEQ ID NO 8
<211> LENGTH: 38
<212> TYPE: PRT
<213> ORGANISM: Artificial Sequence
<220> FEATURE:
<223> OTHER INFORMATION: Description of Artificial Sequence:Consensus
      sequence derived from staphylococcal and
      streptococcal toxins

<400> SEQUENCE: 8

Cys Met Tyr Gly Gly Val Thr Glu His Glu Gly Asn Lys Lys Asn Val
 1               5                  10                  15

Thr Val Gln Glu Leu Asp Tyr Lys Ile Arg Lys Tyr Leu Val Asp Asn
            20                  25                  30

Lys Lys Leu Tyr Gly Cys
        35

<210> SEQ ID NO 9
<211> LENGTH: 12
<212> TYPE: PRT
<213> ORGANISM: Staphylococcus

<400> SEQUENCE: 9

Cys Met Tyr Gly Gly Val Thr Leu His Asp Asn Asn
 1               5                  10

<210> SEQ ID NO 10
<211> LENGTH: 12
<212> TYPE: PRT
<213> ORGANISM: Staphylococcus

<400> SEQUENCE: 10

Cys Met Tyr Gly Gly Val Thr Glu His Asn Gly Asn
 1               5                  10

<210> SEQ ID NO 11
<211> LENGTH: 12
<212> TYPE: PRT
<213> ORGANISM: Staphylococcus

<400> SEQUENCE: 11

Cys Met Tyr Gly Gly Ile Thr Lys His Glu Gly Asn
 1               5                  10

<210> SEQ ID NO 12
<211> LENGTH: 12
<212> TYPE: PRT
<213> ORGANISM: Staphylococcus

<400> SEQUENCE: 12
```

```
Cys Thr Tyr Gly Gly Val Thr Pro His Glu Gly Asn
 1               5                  10
```

<210> SEQ ID NO 13
<211> LENGTH: 12
<212> TYPE: PRT
<213> ORGANISM: Staphylococcus

<400> SEQUENCE: 13

```
Cys Met Tyr Gly Gly Val Thr Leu His Asp Asn Asn
 1               5                  10
```

<210> SEQ ID NO 14
<211> LENGTH: 11
<212> TYPE: PRT
<213> ORGANISM: Staphylococcus

<400> SEQUENCE: 14

```
Cys Leu Tyr Gly Gly Ile Thr Leu Asn Ser Glu
 1               5                  10
```

<210> SEQ ID NO 15
<211> LENGTH: 12
<212> TYPE: PRT
<213> ORGANISM: Streptococcus

<400> SEQUENCE: 15

```
Cys Ile Tyr Gly Gly Val Thr Asn His Glu Gly Asn
 1               5                  10
```

<210> SEQ ID NO 16
<211> LENGTH: 12
<212> TYPE: PRT
<213> ORGANISM: Streptococcus

<400> SEQUENCE: 16

```
Tyr Ile Tyr Gly Gly Ile Thr Pro Ala Gln Asn Asn
 1               5                  10
```

<210> SEQ ID NO 17
<211> LENGTH: 12
<212> TYPE: PRT
<213> ORGANISM: Streptococcus

<400> SEQUENCE: 17

```
Cys Met Tyr Gly Gly Val Thr Glu His His Arg Asn
 1               5                  10
```

<210> SEQ ID NO 18
<211> LENGTH: 24
<212> TYPE: PRT
<213> ORGANISM: Staphylococcus

<400> SEQUENCE: 18

```
Lys Lys Asn Val Thr Val Gln Glu Leu Asp Leu Gln Ala Arg Arg Tyr
 1               5                  10                  15

Leu Gln Glu Lys Tyr Asn Leu Tyr
                20
```

<210> SEQ ID NO 19
<211> LENGTH: 24
<212> TYPE: PRT
<213> ORGANISM: Staphylococcus

<400> SEQUENCE: 19

```
Lys Lys Lys Val Thr Ala Gln Glu Leu Asp Tyr Leu Thr Arg His Tyr
  1               5                   10                  15

Leu Val Lys Asn Lys Lys Leu Tyr
              20
```

<210> SEQ ID NO 20
<211> LENGTH: 24
<212> TYPE: PRT
<213> ORGANISM: Staphylococcus

<400> SEQUENCE: 20

```
Lys Lys Ser Val Thr Ala Gln Glu Leu Asp Ile Lys Ala Arg Asn Phe
  1               5                   10                  15

Leu Ile Asn Lys Lys Asn Leu Tyr
              20
```

<210> SEQ ID NO 21
<211> LENGTH: 24
<212> TYPE: PRT
<213> ORGANISM: Staphylococcus

<400> SEQUENCE: 21

```
Lys Lys Asn Val Thr Val Gln Glu Leu Asp Ala Gln Ala Arg Arg Tyr
  1               5                   10                  15

Leu Gln Lys Asp Leu Lys Leu Tyr
              20
```

<210> SEQ ID NO 22
<211> LENGTH: 24
<212> TYPE: PRT
<213> ORGANISM: Staphylococcus

<400> SEQUENCE: 22

```
Lys Lys Glu Val Thr Val Gln Glu Leu Asp Leu Gln Ala Arg His Tyr
  1               5                   10                  15

Leu His Gly Lys Phe Gly Leu Tyr
              20
```

<210> SEQ ID NO 23
<211> LENGTH: 24
<212> TYPE: PRT
<213> ORGANISM: Staphylococcus

<400> SEQUENCE: 23

```
Lys Lys Asn Val Thr Leu Gln Glu Leu Asp Ile Lys Ile Arg Lys Ile
  1               5                   10                  15

Leu Ser Asp Lys Tyr Lys Ile Tyr
              20
```

<210> SEQ ID NO 24
<211> LENGTH: 24
<212> TYPE: PRT
<213> ORGANISM: Streptococcus

<400> SEQUENCE: 24

```
Lys Lys Met Val Thr Ala Gln Glu Leu Asp Tyr Lys Val Arg Lys Tyr
  1               5                   10                  15

Leu Thr Asp Asn Lys Gln Leu Tyr
              20
```

<210> SEQ ID NO 25

```
<211> LENGTH: 24
<212> TYPE: PRT
<213> ORGANISM: Streptococcus

<400> SEQUENCE: 25

Lys Asp Ile Val Thr Phe Gln Glu Ile Asp Phe Lys Ile Arg Lys Leu
 1               5                  10                  15

Tyr Met Asp Asn Tyr Lys Ile Tyr
            20

<210> SEQ ID NO 26
<211> LENGTH: 24
<212> TYPE: PRT
<213> ORGANISM: Streptococcus

<400> SEQUENCE: 26

Lys Lys Gln Val Thr Val Gln Glu Leu Asp Cys Lys Thr Arg Lys Ile
 1               5                  10                  15

Leu Val Ser Arg Lys Asn Leu Tyr
            20

<210> SEQ ID NO 27
<211> LENGTH: 24
<212> TYPE: PRT
<213> ORGANISM: Staphylococcus

<400> SEQUENCE: 27

Lys Lys Gln Leu Ala Ile Ser Thr Leu Asp Phe Glu Ile Arg His Gln
 1               5                  10                  15

Leu Thr Gln Ile His Gly Leu Tyr
            20

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence:Consensus
      sequence derived from staphylococcal and
      streptococcal toxins
<221> NAME/KEY: UNSURE
<222> LOCATION: (1)..(2)
<223> OTHER INFORMATION: XAA may be any amino acid or no amino acid
<221> NAME/KEY: UNSURE
<222> LOCATION: (6)
<223> OTHER INFORMATION: XAA may be L, I or V
<221> NAME/KEY: UNSURE
<222> LOCATION: (8)
<223> OTHER INFORMATION: XAA may be any amino acid
<221> NAME/KEY: UNSURE
<222> LOCATION: (9)
<223> OTHER INFORMATION: XAA may be any amino acid or no amino acid
<221> NAME/KEY: UNSURE
<222> LOCATION: (10)..(11)
<223> OTHER INFORMATION: XAA may be any amino acid

<400> SEQUENCE: 28

Xaa Xaa Tyr Gly Gly Xaa Thr Xaa Xaa Xaa Xaa Asn
 1               5                  10

<210> SEQ ID NO 29
<211> LENGTH: 24
<212> TYPE: PRT
<213> ORGANISM: Artificial Sequence
<220> FEATURE:
<223> OTHER INFORMATION: Description of Artificial Sequence:Consensus
      sequence derived from staphylococcal and
      streptococcal toxins
```

```
<221> NAME/KEY: UNSURE
<222> LOCATION: (11)..(13)
<223> OTHER INFORMATION: XAA may be any amino acid
<221> NAME/KEY: UNSURE
<222> LOCATION: (2)..(3)
<223> OTHER INFORMATION: XAA may be any amino acid
<221> NAME/KEY: UNSURE
<222> LOCATION: (4)
<223> OTHER INFORMATION: XAA may be L, I or V
<221> NAME/KEY: UNSURE
<222> LOCATION: (5)..(8)
<223> OTHER INFORMATION: XAA may be any amino acid
<221> NAME/KEY: UNSURE
<222> LOCATION: (9)
<223> OTHER INFORMATION: XAA may be L, I or V
<221> NAME/KEY: UNSURE
<222> LOCATION: (15)..(16)
<223> OTHER INFORMATION: XAA may be any amino acid
<221> NAME/KEY: UNSURE
<222> LOCATION: (17)
<223> OTHER INFORMATION: XAA may be L or Y
<221> NAME/KEY: UNSURE
<222> LOCATION: (18)..(22)
<223> OTHER INFORMATION: XAA may be any amino acid
<221> NAME/KEY: UNSURE
<222> LOCATION: (23)
<223> OTHER INFORMATION: XAA may be L, I or V

<400> SEQUENCE: 29

Lys Xaa Xaa Xaa Xaa Xaa Xaa Xaa Asp Xaa Xaa Xaa Arg Xaa Xaa
 1               5                  10                  15

Xaa Xaa Xaa Xaa Xaa Xaa Xaa Tyr
            20

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence:Consensus
      sequence derived from staphylococcal and
      streptococcal toxins
<221> NAME/KEY: UNSURE
<222> LOCATION: (6)
<223> OTHER INFORMATION: XAA may be V or I; preferably V
<221> NAME/KEY: UNSURE
<222> LOCATION: (8)
<223> OTHER INFORMATION: XAA may be L, E, K, P or N; preferably E or L
<221> NAME/KEY: UNSURE
<222> LOCATION: (10)
<223> OTHER INFORMATION: XAA may be D, N, E, Q or H; preferably E

<400> SEQUENCE: 30

Cys Met Tyr Gly Gly Xaa Thr Xaa His Xaa Gly Asn
 1               5                  10

<210> SEQ ID NO 31
<211> LENGTH: 24
<212> TYPE: PRT
<213> ORGANISM: Artificial Sequence
<220> FEATURE:
<221> NAME/KEY: UNSURE
<222> LOCATION: (11)
<223> OTHER INFORMATION: XAA may be L, Y, I, A, F or C; preferably Y
<221> NAME/KEY: UNSURE
<222> LOCATION: (3)
<223> OTHER INFORMATION: XAA may be N, K, S, E, M, I or Q; preferably N
<221> NAME/KEY: UNSURE
<222> LOCATION: (6)
<223> OTHER INFORMATION: XAA may be V, A, L, F or I; preferably V
<221> NAME/KEY: UNSURE
<222> LOCATION: (15)
<223> OTHER INFORMATION: XAA may be R, H, N or K; preferably K
<221> NAME/KEY: UNSURE
```

```
<222> LOCATION: (16)
<223> OTHER INFORMATION: XAA may be Y, F, I, L or Q; preferably Y
<221> NAME/KEY: UNSURE
<222> LOCATION: (17)
<223> OTHER INFORMATION: XAA may be L or Y; preferably L
<221> NAME/KEY: UNSURE
<222> LOCATION: (12)
<223> OTHER INFORMATION: XAA may be Q, L, K or E; preferably K
<221> NAME/KEY: UNSURE
<222> LOCATION: (13)
<223> OTHER INFORMATION: XAA may be A, T, I or V; preferably I
<221> NAME/KEY: UNSURE
<222> LOCATION: (18)
<223> OTHER INFORMATION: XAA may be Q, V, I, H, S, T or M; preferably V
<221> NAME/KEY: UNSURE
<222> LOCATION: (19)
<223> OTHER INFORMATION: XAA may be E, K, N, D, G, S or Q; preferably D
<221> NAME/KEY: UNSURE
<222> LOCATION: (20)
<223> OTHER INFORMATION: XAA may be K, N, D, R or I; preferably N
<221> NAME/KEY: UNSURE
<222> LOCATION: (21)
<223> OTHER INFORMATION: XAA may be Y, K, L, F or H; preferably K
<221> NAME/KEY: UNSURE
<222> LOCATION: (22)
<223> OTHER INFORMATION: XAA may be N, K, G or Q; preferably K
<223> OTHER INFORMATION: Description of Artificial Sequence: Consensus
      Sequence derived from staphylococcal and
      streptococcal toxins

<400> SEQUENCE: 31

Lys Lys Xaa Val Thr Xaa Gln Glu Leu Asp Xaa Xaa Xaa Arg Xaa Xaa
 1               5                  10                  15

Xaa Xaa Xaa Xaa Xaa Xaa Leu Tyr
            20

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 32

Cys Met Tyr Gly Gly Val Thr Leu His Asp Gly Asn
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 33

Cys Met Tyr Gly Gly Val Thr Leu His Asn Gly Asn
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 34

Cys Met Tyr Gly Gly Val Thr Leu His Glu Gly Asn
 1               5                  10
```

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 35

Cys Met Tyr Gly Gly Val Thr Leu His Gln Gly Asn
 1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 36

Cys Met Tyr Gly Gly Val Thr Leu His His Gly Asn
 1               5                  10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 37

Cys Met Tyr Gly Gly Val Thr Glu His Asp Gly Asn
 1               5                  10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: SEB

<400> SEQUENCE: 38

Cys Met Tyr Gly Gly Val Thr Glu His Asn Gly Asn
 1               5                  10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 39

Cys Met Tyr Gly Gly Val Thr Glu His Gln Gly Asn
 1               5                  10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins -continued

```
<400> SEQUENCE: 40

Cys Met Tyr Gly Gly Val Thr Glu His His Gly Asn
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 41

Cys Met Tyr Gly Gly Val Thr Lys His Asp Gly Asn
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 42

Cys Met Tyr Gly Gly Val Thr Lys His Asn Gly Asn
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 43

Cys Met Tyr Gly Gly Val Thr Lys His Glu Gly Asn
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 44

Cys Met Tyr Gly Gly Val Thr Lys His Gln Gly Asn
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 45

Cys Met Tyr Gly Gly Val Thr Lys His His Gly Asn
1               5                   10

<210> SEQ ID NO 46
<211> LENGTH: 12
<212> TYPE: PRT
```

```
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 46

Cys Met Tyr Gly Gly Val Thr Pro His Asp Gly Asn
  1               5                  10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 47

Cys Met Tyr Gly Gly Val Thr Pro His Asn Gly Asn
  1               5                  10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 48

Cys Met Tyr Gly Gly Val Thr Pro His Glu Gly Asn
  1               5                  10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 49

Cys Met Tyr Gly Gly Val Thr Pro His Gln Gly Asn
  1               5                  10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 50

Cys Met Tyr Gly Gly Val Thr Pro His His Gly Asn
  1               5                  10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 51

Cys Met Tyr Gly Gly Val Thr Asn His Asp Gly Asn
  1               5                  10
```

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 52

Cys Met Tyr Gly Gly Val Thr Asn His Asn Gly Asn
 1               5                  10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 53

Cys Met Tyr Gly Gly Val Thr Asn His Glu Gly Asn
 1               5                  10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 54

Cys Met Tyr Gly Gly Val Thr Asn His Gln Gly Asn
 1               5                  10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 55

Cys Met Tyr Gly Gly Val Thr Asn His His Gly Asn
 1               5                  10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 56

Cys Met Tyr Gly Gly Ile Thr Leu His Asp Gly Asn
 1               5                  10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

```
<400> SEQUENCE: 57

Cys Met Tyr Gly Gly Ile Thr Leu His Asn Gly Asn
  1               5                  10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 58

Cys Met Tyr Gly Gly Ile Thr Leu His Glu Gly Asn
  1               5                  10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 59

Cys Met Tyr Gly Gly Ile Thr Leu His Gln Gly Asn
  1               5                  10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 60

Cys Met Tyr Gly Gly Ile Thr Leu His His Gly Asn
  1               5                  10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 61

Cys Met Tyr Gly Gly Ile Thr Glu His Asp Gly Asn
  1               5                  10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 62

Cys Met Tyr Gly Gly Ile Thr Glu His Asn Gly Asn
  1               5                  10

<210> SEQ ID NO 63
<211> LENGTH: 12
```

```
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 63

Cys Met Tyr Gly Gly Ile Thr Glu His Glu Gly Asn
  1               5                  10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 69

Cys Met Tyr Gly Gly Ile Thr Lys His Gly Gly Asn
 1               5                  10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 70

Cys Met Tyr Gly Gly Ile Thr Lys His His Gly Asn
 1               5                  10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 71

Cys Met Tyr Gly Gly Ile Thr Pro His Asp Gly Asn
 1               5                  10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 72

Cys Met Tyr Gly Gly Ile Thr Pro His Asn Gly Asn
 1               5                  10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

<400> SEQUENCE: 73

Cys Met Tyr Gly Gly Ile Thr Pro His Glu Gly Asn
 1               5                  10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Variants
      of staphylococcal and streptococcal toxins

```
<400> SEQUENCE: 74

Cys Met Tyr Gly Gly Ile Thr Pro His Gln Gly Asn
 1               5                  10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 75

Cys Met Tyr Gly Gly Ile Thr Pro His His Gly Asn
 1               5                  10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 76

Cys Met Tyr Gly Gly Ile Thr Asn His Asp Gly Asn
 1               5                  10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 77

Cys Met Tyr Gly Gly Ile Thr Asn His Asn Gly Asn
 1               5                  10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 78

Cys Met Tyr Gly Gly Ile Thr Asn His Glu Gly Asn
 1               5                  10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 79

Cys Met Tyr Gly Gly Ile Thr Asn His Gln Gly Asn
 1               5                  10

<210> SEQ ID NO 80
<211> LENGTH: 12
```

```
<212> TYPE: PRT
<213> ORGANISM: Artificial Sequence
<220> FEATURE:
<223> OTHER INFORMATION: Description of Artificial Sequence:  Variants
      of staphylococcal and streptococcal toxins

<400> SEQUENCE: 80

Cys Met Tyr Gly Gly Ile Thr Asn His His Gly Asn
  1               5                  10
```